United States Patent [19]
Majer et al.

[11] Patent Number: 5,849,691
[45] Date of Patent: Dec. 15, 1998

[54] PEPTIDOMIMETIC INHIBITORS OF CATHEPSIN D AND PLASMEPSINS I AND II

[75] Inventors: Pavel Majer; Jack Collins; Sergei Gulnik; John Erickson, all of Frederick, Md.

[73] Assignee: The United States of America as represented by the Department of Health and Human Services, Washington, D.C.

[21] Appl. No.: 603,737

[22] Filed: Feb. 20, 1996

[51] Int. Cl.⁶ .............................. A61K 38/00; C07K 5/12

[52] U.S. Cl. .................................. 514/9; 514/11; 530/317

[58] Field of Search .......................... 514/9, 11; 424/177; 530/317

[56] References Cited

U.S. PATENT DOCUMENTS

| | | | |
|---|---|---|---|
| 4,477,441 | 10/1984 | Boger et al. | 424/177 |
| 4,485,099 | 11/1984 | Boger et al. | 424/177 |

FOREIGN PATENT DOCUMENTS

| | | |
|---|---|---|
| 0401675A1 | 12/1990 | European Pat. Off. . |
| 0401676A1 | 12/1990 | European Pat. Off. . |
| 0443559A2 | 8/1991 | European Pat. Off. . |
| 0443573A2 | 8/1991 | European Pat. Off. . |
| 0566237A2 | 10/1993 | European Pat. Off. . |
| 652009A1 | 5/1995 | European Pat. Off. . |

OTHER PUBLICATIONS

International Search Report, PCT/US97/02930.
Agarwal, Nirankar and Rich, Daniel, 1986, "Inhibition of Cathepsin D by Substrate Analogues Containing Statine and by Analogues of Pepstatin", J. Med. Chem., vol. 29 pp. 2519–2524.
Reily, Michael, et al., 1992, "Design, synthesis and solution structure of a renin inhibtor", Federation of European Biochemical Societies, vol. 302 (1), pp. 97–103.
Wu, H. et al., 1994, "The Structure of Qingjingmycin A Novel Peptide–Type Metabolite of a Hybrid Strain FM3–32 Derived from *Streptomyces Qingfengmyceticus* and *S. hydroscopius* var. *jinggangensis*", National Product Letters, vol. 5, pp. 89–93.
Maibaum, Juergen and Rich, Daniel, 1988, "Inhibition of Porcine Pepsin by Two Substrate Analogues Containing Statine. The Effect of Histidine at the P2 Subsite on the Inhibition of Aspartic Proteinases", J. Med. Chem. vol. 31, pp. 625–629.

*Primary Examiner*—Cecilia J. Tsang
*Assistant Examiner*—Bennett Celsa
*Attorney, Agent, or Firm*—Spencer & Frank

[57] ABSTRACT

The present invention relates to the design and synthesis of linear and cyclic inhibitors of cathepsin D and plasmepsins I and II. The present invention also relates to the uses of these inhibitors for inhibiting invasion and metastasis of cancerous cells. The present invention further relates to the use of cathepsin D and plasmepsin I and II inhibitors for the prevention and treatment of Alzheimer's disease and malaria.

10 Claims, No Drawings

SEQUENCE LISTING ( 1 ) GENERAL INFORMATION:

( i i i ) NUMBER OF SEQUENCES: 39

( 2 ) INFORMATION FOR SEQ ID NO:1:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal fragment ( i x ) FEATURE:
        ( A ) NAME/KEY:
        ( B ) LOCATION:
        ( C ) IDENTIFICATION METHOD:
        ( D ) OTHER INFORMATION: Isovaleryl is positioned at the amino terminus. Xaa
is statine.

(xi) SEQUENCE DESCRIPTION:SEQ ID NO:1:

Val  Val  Xaa  Val  Leu  Gly
     1                     5

(2) INFORMATION FOR SEQ ID NO:2:

(i) SEQUENCE CHARACTERISTICS:
      (A) LENGTH: 6
      (B) TYPE: amino acid
      (C) STRANDEDNESS:
      (D) TOPOLOGY: linear (ii) MOLECULE TYPE:
      (A) DESCRIPTION: peptide (iii) HYPOTHETICAL: No (iv) ANTI-SENSE: No (v) FRAGMENT TYPE: C-terminal (ix) FEATURE:
      (A) NAME/KEY:
      (B) LOCATION:
      (C) IDENTIFICATION METHOD:
      (D) OTHER INFORMATION: Isovaleryl is
          positioned at the amino terminus. Xaa
          is statine.

(xi) SEQUENCE DESCRIPTION:SEQ ID NO:2:

Gln  Val  Xaa  Ala  Leu  Gly
     1                     5

(2) INFORMATION FOR SEQ ID NO:3:

(i) SEQUENCE CHARACTERISTICS:
      (A) LENGTH: 6
      (B) TYPE: amino acid
      (C) STRANDEDNESS:
      (D) TOPOLOGY: linear (ii) MOLECULE TYPE:
      (A) DESCRIPTION: peptide (iii) HYPOTHETICAL: No (iv) ANTI-SENSE: No (v) FRAGMENT TYPE: C-terminal (ix) FEATURE:
      (A) NAME/KEY:
      (B) LOCATION:
      (C) IDENTIFICATION METHOD:
      (D) OTHER INFORMATION: Isovaleryl is
          positioned at the amino terminus. Xaa
          is statine.

(xi) SEQUENCE DESCRIPTION:SEQ ID NO:3:

Lys  Val  Xaa  Ala  Leu  Gly
     1                     5

(2) INFORMATION FOR SEQ ID NO:4:

(i) SEQUENCE CHARACTERISTICS:
      (A) LENGTH: 6
      (B) TYPE: amino acid
      (C) STRANDEDNESS:
      (D) TOPOLOGY: linear (ii) MOLECULE TYPE:

(A) DESCRIPTION: peptide (iii) HYPOTHETICAL: No (iv) ANTI-SENSE: No (v) FRAGMENT TYPE: C-terminal (ix) FEATURE:
    (A) NAME/KEY:
    (B) LOCATION:
    (C) IDENTIFICATION METHOD:
    (D) OTHER INFORMATION: t-butylacetyl is positioned at the amino terminus. Xaa is statine.

(xi) SEQUENCE DESCRIPTION:SEQ ID NO:4:

```
Val  Val  Xaa  Ala  Leu  Gly
 1                 5
```

(2) INFORMATION FOR SEQ ID NO:5:

(i) SEQUENCE CHARACTERISTICS:
    (A) LENGTH: 6
    (B) TYPE: amino acid
    (C) STRANDEDNESS:
    (D) TOPOLOGY: linear (ii) MOLECULE TYPE:
    (A) DESCRIPTION: peptide (iii) HYPOTHETICAL: No (iv) ANTI-SENSE: No (v) FRAGMENT TYPE: C-terminal (ix) FEATURE:
    (A) NAME/KEY:
    (B) LOCATION:
    (C) IDENTIFICATION METHOD:
    (D) OTHER INFORMATION: isovaleryl is positioned at the amino terminus. Xaa is statine.

(xi) SEQUENCE DESCRIPTION:SEQ ID NO:5:

```
Val  Ile  Xaa  Ala  Leu  Gly
 1                 5
```

(2) INFORMATION FOR SEQ ID NO:6:

(i) SEQUENCE CHARACTERISTICS:
    (A) LENGTH: 6
    (B) TYPE: amino acid
    (C) STRANDEDNESS:
    (D) TOPOLOGY: linear (ii) MOLECULE TYPE:
    (A) DESCRIPTION: peptide (iii) HYPOTHETICAL: No (iv) ANTI-SENSE: No (v) FRAGMENT TYPE: C-terminal (ix) FEATURE:
    (A) NAME/KEY:
    (B) LOCATION:
    (C) IDENTIFICATION METHOD:
    (D) OTHER INFORMATION: isovaleryl is positioned at the amino terminus. Xaa is statine.

(xi) SEQUENCE DESCRIPTION:SEQ ID NO:6:

Val  Leu  Xaa  Ala  Leu  Gly
            1              5

( 2 ) INFORMATION FOR SEQ ID NO:7:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: t- butylacetyl is
              positioned at the amino terminus. Xaa
              is phenylstatine.

( x i ) SEQUENCE DESCRIPTION:SEQ ID NO:7:

Val  Val  Xaa  Val  Leu  Gly
            1              5

( 2 ) INFORMATION FOR SEQ ID NO:8:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: t- butylacetyl is
              positioned at the amino terminus. Xaa
              is phenylstatine.

( x i ) SEQUENCE DESCRIPTION:SEQ ID NO:8:

Val  Cys  Xaa  Val  Leu  Gly
            1              5

( 2 ) INFORMATION FOR SEQ ID NO:9:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No (v) FRAGMENT TYPE: C-terminal (ix) FEATURE:
    (A) NAME/KEY:
    (B) LOCATION:
    (C) IDENTIFICATION METHOD:
    (D) OTHER INFORMATION: t-butylacetyl is positioned at the amino terminus. Xaa is phenylstatine.

(xi) SEQUENCE DESCRIPTION:SEQ ID NO:9:

Val  Glu  Xaa  Val  Leu  Gly
    1                       5

(2) INFORMATION FOR SEQ ID NO:10:

(i) SEQUENCE CHARACTERISTICS:
        (A) LENGTH: 6
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: t-butylacetyl is positioned at the amino terminus. Xaa is phenylstatine.

(xi) SEQUENCE DESCRIPTION:SEQ ID NO:10:

Val  Asp  Xaa  Val  Leu  Gly
    1                       5

(2) INFORMATION FOR SEQ ID NO:11:

(i) SEQUENCE CHARACTERISTICS:
        (A) LENGTH: 6
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: isovaleryl is positioned at the amino terminus. Xaa is statine.

(xi) SEQUENCE DESCRIPTION:SEQ ID NO:11:

Val  Val  Xaa  Ala  Leu  Gly
    1                       5

(2) INFORMATION FOR SEQ ID NO:12:

(i) SEQUENCE CHARACTERISTICS:
  (A) LENGTH: 6
  (B) TYPE: amino acid
  (C) STRANDEDNESS:
  (D) TOPOLOGY: linear (ii) MOLECULE TYPE:
  (A) DESCRIPTION: peptide (iii) HYPOTHETICAL: No (iv) ANTI-SENSE: No (v) FRAGMENT TYPE: C-terminal (ix) FEATURE:
  (A) NAME/KEY:
  (B) LOCATION:
  (C) IDENTIFICATION METHOD:
  (D) OTHER INFORMATION: t- butylacetyl is
       positioned at the amino terminus. Xaa
       is phenylstatine.

(xi) SEQUENCE DESCRIPTION:SEQ ID NO:12:

```
Val  Cys  Xaa  Val  Cys  Gly
 1                  5
```

(2) INFORMATION FOR SEQ ID NO:13:

(i) SEQUENCE CHARACTERISTICS:
  (A) LENGTH: 4
  (B) TYPE: amino acid
  (C) STRANDEDNESS:
  (D) TOPOLOGY: linear (ii) MOLECULE TYPE:
  (A) DESCRIPTION: peptide (iii) HYPOTHETICAL: No (iv) ANTI-SENSE: No (v) FRAGMENT TYPE: C-terminal (ix) FEATURE:
  (A) NAME/KEY:
  (B) LOCATION:
  (C) IDENTIFICATION METHOD:
  (D) OTHER INFORMATION: Xaa is phenyl
       statine. C2H6CHCH2CO is positioned at
       the amino terminus.

(xi) SEQUENCE DESCRIPTION:SEQ ID NO:13:

```
Val  Val  Val  Xaa
 1
```

(2) INFORMATION FOR SEQ ID NO:14:

(i) SEQUENCE CHARACTERISTICS:
  (A) LENGTH: 5
  (B) TYPE: amino acid
  (C) STRANDEDNESS:
  (D) TOPOLOGY: linear (ii) MOLECULE TYPE:
  (A) DESCRIPTION: peptide (iii) HYPOTHETICAL: No (iv) ANTI-SENSE: No (v) FRAGMENT TYPE: C-terminal (ix) FEATURE:
  (A) NAME/KEY:

(B) LOCATION:
(C) IDENTIFICATION METHOD:
(D) OTHER INFORMATION: Xaa is
phenylstatine. C2H6CHCH2CO is positioned
at the amino terminus.

(xi) SEQUENCE DESCRIPTION:SEQ ID NO:14:

```
Val  Val  Val  Xaa  Val
 1                    5
```

(2) INFORMATION FOR SEQ ID NO:15:

(i) SEQUENCE CHARACTERISTICS:
        (A) LENGTH: 4
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is
phenylstatine. C2H6CHCH2CO is positioned
at the amino terminus.

(xi) SEQUENCE DESCRIPTION:SEQ ID NO:15:

```
Val  Val  Xaa  Val
 1
```

(2) INFORMATION FOR SEQ ID NO:16:

(i) SEQUENCE CHARACTERISTICS:
        (A) LENGTH: 4
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is
phenylstatine. C2H6CHCH2CO is positioned
at the amino terminus.

(xi) SEQUENCE DESCRIPTION:SEQ ID NO:16:

```
Val  Val  Val  Xaa
 1
```

(2) INFORMATION FOR SEQ ID NO:17:

(i) SEQUENCE CHARACTERISTICS:
        (A) LENGTH: 4
        (B) TYPE: amino acid
        (C) STRANDEDNESS:

(D) TOPOLOGY: linear (ii) MOLECULE TYPE:
    (A) DESCRIPTION: peptide (iii) HYPOTHETICAL: No (iv) ANTI-SENSE: No (v) FRAGMENT TYPE: C-terminal (ix) FEATURE:
    (A) NAME/KEY:
    (B) LOCATION:
    (C) IDENTIFICATION METHOD:
    (D) OTHER INFORMATION: Xaa is
        phenylstatine. C2H6CHCH2CO is positioned
        at the amino terminus, and C4H8NOCH2CH2
        is at the carboxy terminus.

(xi) SEQUENCE DESCRIPTION:SEQ ID NO:17:

Val  Val  Val  Xaa
    1

(2) INFORMATION FOR SEQ ID NO:18:

(i) SEQUENCE CHARACTERISTICS:
        (A) LENGTH: 2
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is
            phenylstatine. CH3(CH2)3CO is at the
            amino terminus, and CH3(CH2)4NH is at
            the carboxy terminus.

(xi) SEQUENCE DESCRIPTION:SEQ ID NO:18:

Xaa  Val
        1

(2) INFORMATION FOR SEQ ID NO:19:

(i) SEQUENCE CHARACTERISTICS:
        (A) LENGTH: 5
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is phenylstatine.

( x i ) SEQUENCE DESCRIPTION:SEQ ID NO:19:

His Val Xaa Ala Leu
1               5

( 2 ) INFORMATION FOR SEQ ID NO:20:

( i ) SEQUENCE CHARACTERISTICS:
       ( A ) LENGTH: 5
       ( B ) TYPE: amino acid
       ( C ) STRANDEDNESS:
       ( D ) TOPOLOGY: linear ( i i ) MOLECULE TYPE:
       ( A ) DESCRIPTION: peptide ( i i i ) HYPOTHETICAL: No ( i v ) ANTI-SENSE: No ( v ) FRAGMENT TYPE: C-terminal ( i x ) FEATURE:
       ( A ) NAME/KEY:
       ( B ) LOCATION:
       ( C ) IDENTIFICATION METHOD:
       ( D ) OTHER INFORMATION: Xaa is
             phenylstatine. CH2H6CHCH2CO is
             positioned at the amino terminus.

( x i ) SEQUENCE DESCRIPTION:SEQ ID NO:20:

Val Val Xaa Ala Leu
1               5

( 2 ) INFORMATION FOR SEQ ID NO:21:

( i ) SEQUENCE CHARACTERISTICS:
       ( A ) LENGTH: 4
       ( B ) TYPE: amino acid
       ( C ) STRANDEDNESS:
       ( D ) TOPOLOGY: linear ( i i ) MOLECULE TYPE:
       ( A ) DESCRIPTION: peptide ( i i i ) HYPOTHETICAL: No ( i v ) ANTI-SENSE: No ( v ) FRAGMENT TYPE: C-terminal ( i x ) FEATURE:
       ( A ) NAME/KEY:
       ( B ) LOCATION:
       ( C ) IDENTIFICATION METHOD:
       ( D ) OTHER INFORMATION: Xaa is
             phenylstatine. C2H6NCH2COH is positioned
             at the amino terminus.

( x i ) SEQUENCE DESCRIPTION:SEQ ID NO:21:

Val Xaa Ala Leu
1

( 2 ) INFORMATION FOR SEQ ID NO:22:

( i ) SEQUENCE CHARACTERISTICS:
       ( A ) LENGTH: 4
       ( B ) TYPE: amino acid
       ( C ) STRANDEDNESS:
       ( D ) TOPOLOGY: linear ( i i ) MOLECULE TYPE:
       ( A ) DESCRIPTION: peptide ( i i i ) HYPOTHETICAL: No ( i v ) ANTI-SENSE: No ( v ) FRAGMENT TYPE: C-terminal ( i x ) FEATURE:
    ( A ) NAME/KEY:
    ( B ) LOCATION:
    ( C ) IDENTIFICATION METHOD:
    ( D ) OTHER INFORMATION: Xaa is
        phenylstatine. C5H4NCH2COH is positioned
        at the amino terminus.

( x i ) SEQUENCE DESCRIPTION:SEQ ID NO:22:

Val  Xaa  Ala  Leu
     1

( 2 ) INFORMATION FOR SEQ ID NO:23:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: Xaa is
            phenylstatine. C5H4NCH2COH is positioned
            at the amino terminus.

( x i ) SEQUENCE DESCRIPTION:SEQ ID NO:23:

Val  Xaa  Ala  Leu
         1

( 2 ) INFORMATION FOR SEQ ID NO:24:

( i ) SEQUENCE CHARACTERISTICS:
        ( A ) LENGTH: 4
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: Xaa is
            phenylstatine. C2H6CHOCO is positioned
            at the amino terminus.

( x i ) SEQUENCE DESCRIPTION:SEQ ID NO:24:

Val  Xaa  Ala  Leu (2) INFORMATION FOR SEQ ID NO:25:

(i) SEQUENCE CHARACTERISTICS:
        (A) LENGTH: 5
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is
            phenylstatine. $C_2H_6CHCH_2CO$ is positioned
            at the amino terminus.

(xi) SEQUENCE DESCRIPTION:SEQ ID NO:25:

Val  Val  Xaa  Ala  Leu
         1                            5

(2) INFORMATION FOR SEQ ID NO:26:

(i) SEQUENCE CHARACTERISTICS:
        (A) LENGTH: 5
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No (v) FRAGMENT TYPE: C-terminal (ix) FEATURE:
        (A) NAME/KEY:
        (B) LOCATION:
        (C) IDENTIFICATION METHOD:
        (D) OTHER INFORMATION: Xaa is
            phenylstatine. $C_2H_6CHOCO$ is positioned
            at the amino terminus.

(xi) SEQUENCE DESCRIPTION:SEQ ID NO:26:

Val  Val  Xaa  Ala  Leu
         1                            5

(2) INFORMATION FOR SEQ ID NO:27:

(i) SEQUENCE CHARACTERISTICS:
        (A) LENGTH: 5
        (B) TYPE: amino acid
        (C) STRANDEDNESS:
        (D) TOPOLOGY: linear (ii) MOLECULE TYPE:
        (A) DESCRIPTION: peptide (iii) HYPOTHETICAL: No (iv) ANTI-SENSE: No ( v ) FRAGMENT TYPE: C-terminal ( i x ) FEATURE:
    ( A ) NAME/KEY:
    ( B ) LOCATION:
    ( C ) IDENTIFICATION METHOD:
    ( D ) OTHER INFORMATION: C2H6CHCH2CO is at the amino terminus, and C4H8NOCH2CH2 is at the carboxy terminus.

( x i ) SEQUENCE DESCRIPTION:SEQ ID NO:27:

Val  Val  Xaa  Val  Leu
    1                         5

( 2 ) INFORMATION FOR SEQ ID NO:28:

( i ) SEQUENCE CHARACTERISTICS:
    ( A ) LENGTH: 6
    ( B ) TYPE: amino acid
    ( C ) STRANDEDNESS:
    ( D ) TOPOLOGY: linear ( i i ) MOLECULE TYPE:
    ( A ) DESCRIPTION: peptide ( i i i ) HYPOTHETICAL: No ( i v ) ANTI-SENSE: No ( v ) FRAGMENT TYPE: C-terminal ( i x ) FEATURE:
    ( A ) NAME/KEY:
    ( B ) LOCATION:
    ( C ) IDENTIFICATION METHOD:
    ( D ) OTHER INFORMATION: A cyclic compound, with an amino alkyl substituent at one end, and a carboxy alkyl at the other end. Xaa is phenylstatine.

( x i ) SEQUENCE DESCRIPTION:SEQ ID NO:28:

Val  Phe  Xaa  Val  Cys  Gly
    1                         5

( 2 ) INFORMATION FOR SEQ ID NO:29:

( i ) SEQUENCE CHARACTERISTICS:
    ( A ) LENGTH: 4
    ( B ) TYPE: amino acid
    ( C ) STRANDEDNESS:
    ( D ) TOPOLOGY: linear ( i i ) MOLECULE TYPE:
    ( A ) DESCRIPTION: peptide ( i i i ) HYPOTHETICAL: No ( i v ) ANTI-SENSE: No ( v ) FRAGMENT TYPE: C-terminal ( i x ) FEATURE:
    ( A ) NAME/KEY:
    ( B ) LOCATION:
    ( C ) IDENTIFICATION METHOD:
    ( D ) OTHER INFORMATION: Xaa is phenylstatine.

( x i ) SEQUENCE DESCRIPTION:SEQ ID NO:29:

Val  Phe  Xaa  Val
    1

( 2 ) INFORMATION FOR SEQ ID NO:30:

( i ) SEQUENCE CHARACTERISTICS:
  ( A ) LENGTH: 6
  ( B ) TYPE: amino acid
  ( C ) STRANDEDNESS:
  ( D ) TOPOLOGY: linear ( i i ) MOLECULE TYPE:
  ( A ) DESCRIPTION: peptide ( i i i ) HYPOTHETICAL: No ( i v ) ANTI-SENSE: No ( v ) FRAGMENT TYPE: C-terminal ( i x ) FEATURE:
  ( A ) NAME/KEY:
  ( B ) LOCATION:
  ( C ) IDENTIFICATION METHOD:
  ( D ) OTHER INFORMATION: Xaa is
    phenylstatine.

( x i ) SEQUENCE DESCRIPTION:SEQ ID NO:30:

```
Val  Phe  Xaa  Val  Cys  Gly
 1                   5
```

( 2 ) INFORMATION FOR SEQ ID NO:31:

( i ) SEQUENCE CHARACTERISTICS:
  ( A ) LENGTH: 5
  ( B ) TYPE: amino acid
  ( C ) STRANDEDNESS:
  ( D ) TOPOLOGY: linear ( i i ) MOLECULE TYPE:
  ( A ) DESCRIPTION: peptide ( i i i ) HYPOTHETICAL: No ( i v ) ANTI-SENSE: No ( v ) FRAGMENT TYPE: C-terminal ( i x ) FEATURE:
  ( A ) NAME/KEY:
  ( B ) LOCATION:
  ( C ) IDENTIFICATION METHOD:
  ( D ) OTHER INFORMATION: Xaa is
    phenylstatine.

( x i ) SEQUENCE DESCRIPTION:SEQ ID NO:31:

```
Val  Phe  Xaa  Val  Gly
 1
```

( 2 ) INFORMATION FOR SEQ ID NO:32:

( i ) SEQUENCE CHARACTERISTICS:
  ( A ) LENGTH: 6
  ( B ) TYPE: amino acid
  ( C ) STRANDEDNESS:
  ( D ) TOPOLOGY: linear ( i i ) MOLECULE TYPE:
  ( A ) DESCRIPTION: peptide ( i i i ) HYPOTHETICAL: No ( i v ) ANTI-SENSE: No ( v ) FRAGMENT TYPE: C-terminal ( i x ) FEATURE:
  ( A ) NAME/KEY:
  ( B ) LOCATION:
  ( C ) IDENTIFICATION METHOD:
  ( D ) OTHER INFORMATION: Two Cys substituents are connected by (CH2)2 to form a bridge.
Xaa is phenylstatine ( x i ) SEQUENCE DESCRIPTION:SEQ ID NO:32:

Val Cys Xaa Val Cys Gly
1                5

( 2 ) INFORMATION FOR SEQ ID NO:33:

( i ) SEQUENCE CHARACTERISTICS:
( A ) LENGTH: 6
( B ) TYPE: amino acid
( C ) STRANDEDNESS:
( D ) TOPOLOGY: linear ( i i ) MOLECULE TYPE:
( A ) DESCRIPTION: peptide ( i i i ) HYPOTHETICAL: No ( i v ) ANTI-SENSE: No ( v ) FRAGMENT TYPE: C-terminal ( i x ) FEATURE:
( A ) NAME/KEY:
( B ) LOCATION:
( C ) IDENTIFICATION METHOD:
( D ) OTHER INFORMATION: Two Cys substituents
are connected by (CH2)3 to form a bridge.
Xaa is phenylstatine.

( x i ) SEQUENCE DESCRIPTION:SEQ ID NO:33:

Val Cys Xaa Val Cys Gly
1                5

( 2 ) INFORMATION FOR SEQ ID NO:34:

( i ) SEQUENCE CHARACTERISTICS:
( A ) LENGTH: 6
( B ) TYPE: amino acid
( C ) STRANDEDNESS:
( D ) TOPOLOGY: linear ( i i ) MOLECULE TYPE:
( A ) DESCRIPTION: peptide ( i i i ) HYPOTHETICAL: No ( i v ) ANTI-SENSE: No ( v ) FRAGMENT TYPE: C-terminal ( i x ) FEATURE:
( A ) NAME/KEY:
( B ) LOCATION:
( C ) IDENTIFICATION METHOD:
( D ) OTHER INFORMATION: Two Cys substituents
are connected by (CH2)4 to form a bridge.
Xaa is phenylstatine.

( x i ) SEQUENCE DESCRIPTION:SEQ ID NO:34:

Val Cys Xaa Val Cys Gly
1                5

( 2 ) INFORMATION FOR SEQ ID NO:35:

( i ) SEQUENCE CHARACTERISTICS:
( A ) LENGTH: 6
( B ) TYPE: amino acid
( C ) STRANDEDNESS:
( D ) TOPOLOGY: linear ( i i ) MOLECULE TYPE:

(A) DESCRIPTION: peptide (iii) HYPOTHETICAL: No (iv) ANTI-SENSE: No (v) FRAGMENT TYPE: C-terminal (ix) FEATURE:
 (A) NAME/KEY:
 (B) LOCATION:
 (C) IDENTIFICATION METHOD:
 (D) OTHER INFORMATION: Two Cys substituents
  are connected to a disulfide bridge.
  Xaa is phenylstatine.

(xi) SEQUENCE DESCRIPTION:SEQ ID NO:35:

```
Val  Cys  Xaa  Val  Cys  Gly
 1                 5
```

(2) INFORMATION FOR SEQ ID NO:36:

(i) SEQUENCE CHARACTERISTICS:
  (A) LENGTH: 6
  (B) TYPE: amino acid
  (C) STRANDEDNESS:
  (D) TOPOLOGY: linear (ii) MOLECULE TYPE:
  (A) DESCRIPTION: peptide (iii) HYPOTHETICAL: No (iv) ANTI-SENSE: No (v) FRAGMENT TYPE: C-terminal (ix) FEATURE:
  (A) NAME/KEY:
  (B) LOCATION:
  (C) IDENTIFICATION METHOD:
  (D) OTHER INFORMATION: Amino acids one and
   three are connected. Xaa is
   phenylstatine.

(xi) SEQUENCE DESCRIPTION:SEQ ID NO:36:

```
Xaa  Val  Xaa  Val  Leu  Gly
 1                 5
```

(2) INFORMATION FOR SEQ ID NO:37:

(i) SEQUENCE CHARACTERISTICS:
  (A) LENGTH: 6
  (B) TYPE: amino acid
  (C) STRANDEDNESS:
  (D) TOPOLOGY: linear (ii) MOLECULE TYPE:
  (A) DESCRIPTION: peptide (iii) HYPOTHETICAL: No (iv) ANTI-SENSE: No (v) FRAGMENT TYPE: C-terminal (ix) FEATURE:
  (A) NAME/KEY:
  (B) LOCATION:
  (C) IDENTIFICATION METHOD:
  (D) OTHER INFORMATION: Amino acids one and
   three are connected. Xaa is
   phenylstatine.

(xi) SEQUENCE DESCRIPTION:SEQ ID NO:37:

```
              Xaa  Val  Xaa  Val  Leu  Gly
              1                  5
```

( 2 ) INFORMATION FOR SEQ ID NO:38:

( i ) SEQUENCE CHARACTERISTICS:
        ( A ) LENGTH: 6
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: C2H6CHCH2CO is
            positioned at the amino terminus. Xaa
            is phenylstatine.

( x i ) SEQUENCE DESCRIPTION:SEQ ID NO:38:

```
              Val  Val  Xaa  Ala  Leu  Gly
              1                  5
```

( 2 ) INFORMATION FOR SEQ ID NO:39:

( i ) SEQUENCE CHARACTERISTICS:
        ( A ) LENGTH: 5
        ( B ) TYPE: amino acid
        ( C ) STRANDEDNESS:
        ( D ) TOPOLOGY: linear ( i i ) MOLECULE TYPE:
        ( A ) DESCRIPTION: peptide ( i i i ) HYPOTHETICAL: No ( i v ) ANTI-SENSE: No ( v ) FRAGMENT TYPE: C-terminal ( i x ) FEATURE:
        ( A ) NAME/KEY:
        ( B ) LOCATION:
        ( C ) IDENTIFICATION METHOD:
        ( D ) OTHER INFORMATION: C2H6CHCH2CO is
            positioned at the amino terminus. Xaa
            is phenylstatine.

( x i ) SEQUENCE DESCRIPTION:SEQ ID NO:39:

```
              Val  Xaa  Ala  Leu  Gly
              1             5
```

PEPTIDOMIMETIC INHIBITORS OF CATHEPSIN D AND PLASMEPSINS I AND II

FIELD OF THE INVENTION

The invention relates to linear and cyclic inhibitor compounds of cathepsin D and plasmepsins I and II, and the use of these compounds for the prevention and treatment of diseases, and the like.

BACKGROUND OF THE INVENTION

Human cathepsin D is an intracellular aspartic protease normally found in lysozymes of all cells. The main physiological action of cathepsin D is degradation of cellular and phagocytosed proteins. Cathepsin D has also been implicated in a number of diseases. Elevated levels of cathepsin D have been correlated with poor prognosis in breast cancer. It has also been correlated with increase cell invasion and increased risk of metastasis, as well as shorter relapse-free survival. (See Rochefort, H., *Semin. Cancer Biol.* 1:153 (1990) and Tandon, A. K. et al. *N. Eng. J. Med.* 322, 297 (1990)). The increased level of secretion of cathepsin D in breast cancer cells is due to both overexpression of the gene and altered processing of the protein. High levels of cathepsin D and other proteases, such as collagenase, produced in the vicinity of the growing tumor may degrade the extracellular matrix and thereby promote the escape of cancer cells to the lymphatic and circulatory systems and enhance the invasion of new tissues. (Liotta L. A., *Scientific American* Feb:54 (1992); and Liotta L. A. and Stetler-Stevenson W. G., *Cancer Biol.* 1:99 (1990)). Most deaths incurred from cancer are due to its metastatic spread to secondary organs, therefore an inhibitor of metastasis would have widespread therapeutic use.

Cathepsin D is also believed to be associated with degenerative brain changes, such as those associated with Alzheimer's disease. Cathepsin D is associated with cleavage of amyloid-β-protein precursor, (Cataldo, A. M. et al., *Proc. Natl. Acad. Sci.* 87:3861(1990)) including a mutant precursor that enhances amyloid protein production in transfected cells (Ladror, U. S., et al. *J. Biol. Chem.* 269:18422 (1994)). The amyloid-β-protein that results from proteolysis of the amyloid-β-protein precursor leads to senile plaque formation in brains and may be responsible for Alzheimer's disease. Recently elevated levels of cathepsin D have been found in cerebrospinal fluid in Alzheimer's patients (Schwager, A. L., et al. *J. Neurochem.* 64:443 (1995).

There is little known about substrate specificity and specific inhibitors for cathepsin D (Agarwal, N. S. and Rich, D. H., *J. Med. Chem.* 29:2519 (1986); Jupp, R. A. et al., *Biochem. J.* 265:871 (1990); Scarborough, P. E. et al., *Protein Science* 2:264 (1993); Baldwin, E. T. et al., *Proc. Natl. Acad. Sci.* 90:6796 (1993)).

Accordingly, there is a need for the synthesis of compounds which are specific for the inhibition of the activity of cathepsin D and which may be used in the treatment of metastatic disease and Alzheimer's disease.

A number of cathepsin D inhibitors have been reported (Lin, T. Y. and Williams, H. R., *J. Biol. Chem.* 25:11875 (1970)). Agarwal and Rich reported the design and synthesis of cathepsin D inhibitors wherein the scissile dipeptide unit in a substrate sequence was replaced with a statine (Sta) residue or by a phenylstatine (Pst) unit. (Agarwal, N. S. and Rich, D. H., *J. Med. Chem.* 29:2519 (1986)). Further, Agarwal and Rich evaluated the inhibition of cathepsin D by various analogues of pepstatin, finding that the fragment spanning $P_4$ to $P'_3$ is necessary for the maximum inhibition of bovine cathepsin D.

U.S. Pat. No. 4,746,648 describes peptide derivatives, modeled on the basis of pepstatin, which inhibit renin and acid protease. Tamburini et al., EP 0 569 777 A2 relates to the use of cathepsin D inhibitors for Alzheimer's disease. Patents relating to cyclic peptide inhibitors of renin include Boger et al., U.S. Pat. No. 4,489,099 and Watkins, U.S. Patent No. 4,906,613.

Cyclizing peptidomimetics can increase binding to a target enzyme due to preorganization into the desired conformation. Additionally, such macrocycles offer increased stability against proteolytic cleavage. An area where this approach has been extensively explored is that of renin inhibitors, where various cycles connecting different positions were introduced. The most successful approach was cyclizing from the $P_2$ to $P'_1$ position to generate a series of potent, orally bioavailable renin inhibitors (Weber, A. E. et al. *J. Med. Chem.* 34:2692 (1991); Dhanoa, D. S. et al. *Tet. Lett.* 33:1725 (1992); Weber, A. E. et al. *J. Med. Chem.* 35:3755 (1992); Yang, L. et al. *Tet. Lett.* 34:7035 (1993)). Cyclization of $P_4$ to $P_2$ also gave potent renin inhibitors (Sham, H. L. et al. *J. Chem. Soc. Chem. Commun.* 666 (1990); Thaisrivongs, S. et al. *J. Med. Chem.* 34:1276 (1991)). Some other cycles have been studied (Szewczuk, Z. et al. *Int J. Pept. Prot. Res.* 40:233 (1992); Sham, H. L. et al. *J. Med. Chem.* 31:284 (1988); Dutta, A. S. et al. *J. Med. Chem.* 33:2552 and 2560 (1990)), but the only example of which we are aware of a $P_2$ to $P'_3$ bridge in an aspartyl protease inhibitor is a simple disulfide (Boger, J. Peptides 1983, pp. 569–578, Proceedings of the 8th American Peptide Symposium).

The cyclic compounds described herein differ significantly from this prior art. Many of the compounds incorporate a $P_2$ to $P'_3$ cycle where the scissile bond isostere is part of the ring. Since the macrocycle spans a large portion of the binding cleft, activity is retained after truncation to remove the exocyclic backbone extension. This has the dual advantages of decreasing molecular weight and removing the residues most subject to metabolic cleavage.

Modeling studies reveal that the active sites of the aspartic hemoglobinases (Plasmepsins I and II) from *Plasmodium falciparum* are highly homologous with that of human cathepsin D. Goldberg, et al. isolated and characterized plasmepsins I and II, aspartic proteases responsible for the initial cleavage of hemoglobin that occurs inside the protozoan Plasmodium's digestive vacuole (Goldberg, D. E. et al., *J. Exp. Med.* 173:961 (1991), Hill, J. et al. *FEBS Letters* 352:155 (1994)). Protozoans of the genus Plasmodium are the causative agents of malaria. The cleavage of hemoglobin by plasmepsins I and II occurs at sites within the hemoglobin sequence that are conserved in human hemoglobins. These cleavage events are essential for the conformational breakdown of hemoglobin that enables its subsequent cleavage by a series of other proteolytic enzymes. The digested hemoglobin is a primary nutrition source for the malarial parasite, which cannot grow in the absence of functional hemoglobinases. Goldberg has demonstrated that inhibitors of plasmepsins can kill the parasite in a cell culture of infected human erythrocytes (Goldberg, D. E. et al., *EMBO J.* 13:306 (1994), Gluzman, I. Y. et al. *J. Clin. Invest.* 93:1602 (1994))

Therefore, there is a need for cathepsin D inhibitors in the treatment of Alzheimer's disease, cancer, and for aiding in the further elucidation of the roles of cathepsin D in human diseases and a need for plasmepsin inhibitors to treat malaria.

It is an object of the present invention to provide cathepsin D and plasmepsin I and II inhibitors for use in the treatment of metastatic disease, for use in the inhibition of cleavage of β-amyloid precursors and for the prevention of progressive neurological dysfunction in Alzheimer's disease, as well as for the prevention of the growth of Plasmodium parasites including *Plasmodium falciparum*, the most deadly cause of malaria.

SUMMARY OF THE INVENTION

The present invention relates to cathepsin D and plasmepsin I and II inhibitor compounds and their use as pharmaceutically active agents. The present invention further provides for uses of these inhibitors for the prevention and treatment of diseases, such as, for example, cancer, Alzheimer's disease, and malaria.

Specifically, the present invention provides for novel linear compounds as well as branched and cyclic analogs of these compounds which are inhibitors of cathepsin D and which exhibit inhibitory potency against plasmepsins I and II. Further, the present invention relates to novel related cyclic compounds which are cathepsin D and plasmepsin I and II inhibitors.

The present invention also provides for pharmaceutical compositions comprising effective amounts of at least one of the present inhibitors for use in the prevention and treatment of diseases, such as cancer, Alzheimer's disease, and malaria.

Specifically, the present invention provides for pharmaceutical compositions which decrease the levels of activity of cathepsin D present in a subject, thereby inhibiting cancer cell invasion and metastasis.

The present invention also provides for pharmaceutical compositions comprising at least one of the present inhibitors for the treatment and prevention of Alzheimer's disease which decrease the occurrence of cleavage of amyloid-β-protein precursors and senile plaque formation in a subject.

Further, the present invention provides for pharmaceutical compositions which inhibit plasmepsin I or II or both and prevent hemoglobin degradation and are thus useful in the treatment of malaria.

These and other features of the invention will be better understood through the following detailed description of the invention. The scope of the invention is limited only through the claims appended hereto.

DETAILED DESCRIPTION OF THE INVENTION

The present invention relates to compounds of formula (I):

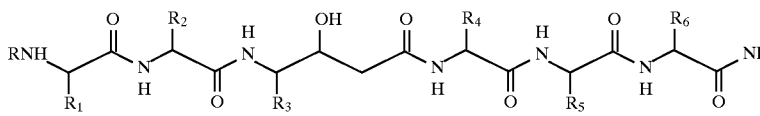

in which R, $R_7$ =represent hydrogen, alkoxycarbonyl, aralkoxycarbonyl, alkylcarbonyl, cycloalkylcarbonyl, cycloalkylalkoxycarbonyl, cycloalkylalkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, mono- and disubstituted aminocarbonyl and mono- and di-substituted aminoalkyl, alkoxyalkyl, akylthioalkyl, mono- and disubstituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is disubstituted, said substituents along with the nitrogen atom to which they are attached form a heterocycloalkyl or heteroaryl radical; $R_1$, $R_2$, $R_4$, $R_5$, R6=the side chain of a residue of an amino acid remaining after formation of a peptide linkage and include optionally substituted lower alkyl, lower cycloalkyl, aryl, aralkyl and heteroaryl; $R_3$ =optionally substituted lower alkyl, lower alkoxy, lower alkylthio, mono or di-lower alkyl amino, aralkyl, aralkoxy, aralkylthio, aralkylamino, cycloalkylalkyl, cycloalkylalkoxy, cycloalkylalkylthio, cycloalkylalkylamino. Also encompassed are compounds where $R_2$ and $R_5$ or $R_1$ and $R_3$ are connected by a bridging moiety having 4–14 atoms comprised of any stable combination of C, N, 0, or S. This chain may be optionally substituted by halo, hydroxy, amino, lower alkyl, lower alkoxy, lower alkylthio, mono or di-lower alkyl amino, oxo, thiono, alkylimino, mono- or dialkylmethylidene, $COR_3$. The bridging group may also be unsaturated so as to include the residues of alkenes, imines, alkynes and allenes. Furthermore, any part of the bridging moiety may comprise part of an optionally substituted aromatic, heteroaromatic, or cycloalkyl ring. Amino acids from which the residues containing $R_1$, $R_2$, $R_4$, $R_5$ and $R_6$ can be derived include glycine, alanine, valine, leucine, isoleucine, serine, threonine, cysteine, methionine, aspartic acid, asparagine, glutamic acid, glutamine, lysine, hydroxylysine, arginine, phenylalanine, tyrosine, tryptophan, and histidine. Useful substituents and the optional substituted $R_1$, $R_2$, $R_4$, $R_5$ and $R_6$ moieties include the functional groups which are attached to the above named aminoacids.

The present invention further relates to compounds of the Formula (II):

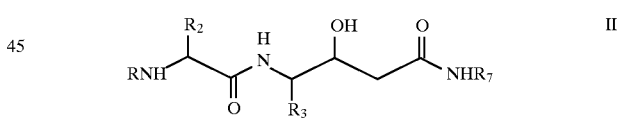

wherein R, $R_2$, $R_3$, $R_7$ are defined as in formula I, or of Formula (III):

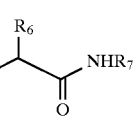

in which R, $R_2$, $R_3$, R4, $R_7$ are defined as in formula I.

The present invention also relates to cyclic compounds of formula (IV):

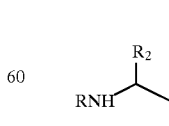

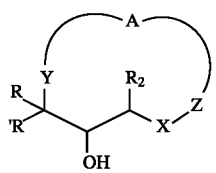

where X=CWNR, S(O)$_n$NR, P(O)(Q)NR; W=O, S, NR; n=0, 1, 2;
Q=R, OR, N(R)$_2$
Y=NRCW, NRS(O)$_n$, NRP(O)(Q)
Z=CRR', NR
A=a bridging group having 2–15 atoms comprised of any stable combination of C, N, O, or S. This bridging group may itself be bridged by one or more chains comprised of C, N, O, or S atoms so as to generate additional rings of 3–7 atoms. The bridging groups may be optionally substituted by OH, NH$_2$, halo, optionally substituted lower alkyl, lower alkoxy, lower alkylthio, mono or di-lower alkyl amino, oxo, thiono, alkylimino, mono- or dialkylmethylidene, COR$_3$. The bridging moiety may also be unsaturated so as to contain portions which are the residues of alkene, imine, alkyne and allene groups. Furthermore, any part of the bridging moiety may comprise part of an optionally substituted aromatic, heteroaromatic, alicyclic, or heterocyclic ring.
R=is as defined hereinabove
R', R$_2$=H, halo, optionally substituted lower alkyl, lower alkoxy, lower alkylthio, mono or di-lower alkyl amino
R$_3$=is as defined hereinabove Also encompassed within the scope of the invention are compounds of formula IVa where IVa has the structure shown for IV and X, Y=NRCW, NRS(O)$_n$, NRP(O)(Q); Z=CRR', NR, O, S and all other definitions are as above.

Additionally contemplated are compounds of the formula IVb where IVb has the structure shown for IV, where X=OCWNR, SCWNR; Y=NRCW, NRS(O)$_n$, NRP(O)(Q); Z=CRR', NR and all other definitions are as above.

The present invention also relates to cyclic compounds of formula (V):

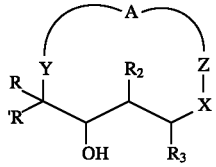

where X=CWNR, S(O)$_n$NR, P(O)(Q)NR; W=O, S, NR; n=0, 1, 2;
Q=R, OR, N(R)$_2$
Y=NRCW, NRS(O)$_n$, NRP(O)(Q)
Z=CRR', NR
A=is as defined hereinabove
R=is as defined hereinabove.
R', R$_2$ and R$_3$=H, halo, optionally substituted lower alkyl, lower alkoxy, lower alkylthio, mono or di-lower alkyl amino.

Also encompassed within the present invention are compounds of formula Va where Va has the structure shown for V and where X, Y=NRCW, NRS(O)$_n$, NRP(O)(Q); Z=CRR', NR, O, S and all other definitions are as above.

Additionally encompassed are compounds of formula Vb where Vb has the structure shown for V and where X=OCWNR, SCWNR; Y=NRCW, NRS(O)$_n$, NRP(O)(Q); Z=CRR', NR and all other definitions are as above.

As utilized herein, the term "alkyl", alone or in combination, means a straight-chain or branched-chain alkyl radical containing from 1 to about 18, preferably from 1 to about 10, carbon atoms. Examples of such radicals include methyl, ethyl, n-propyl, isopropyl, n-butyl, isobutyl, sec-butyl, tert-butyl, amyl, isoamyl, hexyl, octyl and the like. The term "alkenyl", alone or in combination, means a straight-chain or branched-chain hydrocarbon radical having one or more double bonds and containing from 2 to about 18 carbon atoms preferably from 2 to about 10 carbon atoms. Examples of suitable alkenyl radicals include ethenyl, propenyl, allyl, 1,3-butadienyl and the like. The term "alkynyl", alone or in combination, means a straight-chain hydrocarbon or branched chain radical having one or more triple bonds and containing from 2 to about 10 carbon atoms. Examples of alkynyl radicals include ethynyl, propynyl, propargyl, butynyl and the like. The term "alkoxy", alone or in combination, means an alkyl ether radical wherein the term alkyl is as defined above. Examples of suitable alkyl ether radicals include methoxy, ethoxy, n-propoxy, isopropoxy, n-butoxy, iso-butoxy, sec-butoxy, tert-butoxy and the like. The term "cycloalkyl", alone or in combination, means a saturated or partially saturated monocyclic, bicyclic or tricyclic alkyl radical wherein each cyclic moiety contains from about 3 to about 8 carbon atoms. Examples of such cycloalkyl radicals include cyclopropyl, cyclobutyl, cyclopentyl, cyclohexyl and the like. The term "cycloalkylalkyl" means an alkyl radical as defined above which is substituted by a cycloalkyl radical as defined above. Examples of cycloalkylalkyl radicals include cyclopropylmethyl, cyclopropylethyl, cyclohexylmethyl, cyclohexylethyl and the like. The term "aryl", alone or in combination, means an aromatic monocycle or bicyclic or tricyclic such as phenyl, naphthyl, or anthracenyl which optionally carries one or more substituents selected from alkyl, alkoxy, halogen, hydroxy, amino, nitro, cyano, haloalkyl and the like, such as phenyl, p-tolyl, 4-ethoxyphenyl, 4-(tert-butoxy) phenyl, 4-fluorophenyl, 4-chlorophenyl, 4-hydroxyphenyl, 1-naphthyl, 2-naphthyl, and the like. The term "aralkyl", alone or in combination, means an alkyl radical as defined above in which one hydrogen atom is replaced by an aryl radical as defined above, such as benzyl, 2-phenylethyl and the like. The term "aryloxy" means a radical of the formula aryl—O— in which the term aryl has the significance given above. The term "alkanoyl", alone or in combination, means an acyl radical derived from an alkanecarboxylic acid, examples of which include acetyl, propionyl, butyryl, valeryl, 4-methylvaleryl, and the like. The heterocyclyl portion of a heterocyclyl-containing group is a saturated or partially unsaturated monocyclic, bicyclic or tricyclic heterocyle which contains one or more hetero atoms selected from nitrogen, oxygen and sulphur, which is optionally substituted on one or more carbon atoms by halogen, alkyl, alkoxy, oxo, and the like, and/or on a secondary nitrogen atom by alkyl, aralkoxycarbonyl, alkanoyl, aryl or aralkyl or on a tertiary nitrogen atom by oxido and which is attached via a carbon atom. The heteroaryl group is an aromatic monocyclic, bicyclic, or tricyclic heterocycle which contains the hetero atoms and is optionally substituted as defined above with respect to the definition of heterocyclyl. Examples of such heterocyclyl and heteroaryl groups are pyrrolidinyl, piperidinyl, piperazinyl, morpholinyl, thiomorpholinyl, pyrrolyl, imidazolyl (e.g. imidazol 4-yl, 1-benzyloxycarbonylimidazol-4-yl, etc.), pyrazolyl, pyridyl, pyrazinyl, pyrimidinyl, furyl, thienyl, triazolyl, oxazolyl, thiazolyl, indolyl (e.g. 2-indolyl), quinolinyl, (e.g., 3-quinolinyl, 2-quinolinyl, etc.), isoquinolinyl (e.g., 1,2,3, 4-tetrahydro-1-oxo-isoquinolinyl, etc.), quinoxalinyl, B-carbolinyl, benzofuranyl, 1-, 2-, 4- or 5-benzimidazolyl, and the like. The term "aminoalkanoyl" means an acyl group derived from an amino-substituted alkanecarboxylic acid wherein the amino group can be a primary, secondary or tertiary amino group containing substituents selected from hydrogen, alkyl, aryl, aralkyl, cycloalkyl, cycloalkylalkyl radicals and the like. The term "halogen" means fluorine, chlorine, bromine or iodine. The term "haloalkyl" means an alkyl radical having the significance as defined above wherein one or more hydrogens are replaced with a halogen. Examples of such haloalkyl radicals include chloromethyl, 1-bromoethyl, fluoromethyl, difluoromethyl, trifluoromethyl, 1,1,1-trifluoroethyl and the like.

The possible optional substituents mentioned in the hereinabove generic description include at least one alkyl, cycloalkyl, aryl, aralkyl, alkaryl, heteroaryl, alkoxy, halogen, hydroxy, amino, nitro, cyano, haloalkyl wherein the optional substituents may also be optionally substituted and the radicals which are optionally substituted may be singly or multiply substituted with the same or different optional substituents.

The compounds provided by the present invention are advantageous as demonstrated by their activity. Furthermore, the structures of the cyclic compounds of the present invention potentially provide protection of the compounds from enzyme degradation. The low molecular weight and few peptide bonds in these analogs may also contribute to improved bioavailability.

Specific, but non-limiting examples of peptides of Formula (I) useful in the present invention include the following:

|     |                                              | $K_i$ cathepsin D (nM) |
|-----|----------------------------------------------|------------------------|
| (1) | Iva—Val—Val—Sta—Val—Leu—Gly—NH$_2$ (SEQ. ID. NO. 1); | 0.1 |
| (2) | Iva—Gln—Val—Sta—Ala—Leu—Gly—NH$_2$ (SEQ. ID. NO. 2); | 0.35 |
| (3) | Iva—Lys—Val—Sta—Ala—Leu—Gly—NH$_2$ (SEQ. ID. NO. 3); | 3.9 |
| (4) | Tba—Val—Val—Sta—Ala—Leu—Gly—NH$_2$ (SEQ. ID. NO. 4); | 0.04 |
| (5) | Iva—Val—Ile—Sta—Ala—Leu—Gly—NH$_2$ (SEQ. ID. NO. 5); | 0.04 |
| (6) | Iva—Val—Leu—Sta—Ala—Leu—Gly—NH$_2$ (SEQ. ID. NO. 6); | 0.5 |
| (7) | Tba—Val—Val—Pst—Val—Leu—Gly—NH$_2$ (SEQ. ID. NO. 7); | 0.015 |
| (8) | Tba—Val—Cys—Pst—Val—Leu—Gly—NH$_2$ (SEQ. ID. NO. 8); | 0.25 |
| (9) | Tba—Val—Glu—Pst—Val—Leu—Gly—NH$_2$ (SEQ. ID. NO. 9); | 1.25 |
| (10)| Tha—Val—Asp—Pst—Val—Leu—Gly—NH$_2$ (SEQ. ID. NO. 10); | 2.1 |
| (11)| Iva—Val—Val—Sta—Ala—Leu—Gly—NH$_2$ (SEQ. ID. NO. 11); | 0.03 |
| (12)| Tba—Val—Cys—Pst—Val—Cys—Gly—NH$_2$ (SEQ. ID. NO. 12). | 0.66 | which has a PMI $K_i$=32 nM PMII $K_i$=1.7 nM.

Iva=isovaleryl

Tba=t-butylacetyl

Specific, but not limiting examples of peptides of Formula (II) of the present invention include the following:

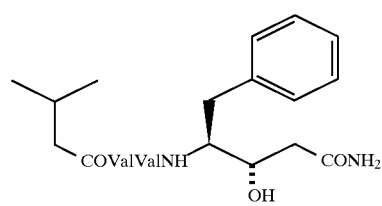

which has a $K_i$ of 800 nM, (SEQ. ID. NO. 13);

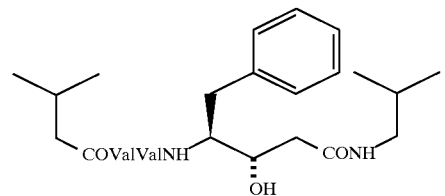

which has a $K_i$ of 12 nM, (SEQ. ID. NO. 14);

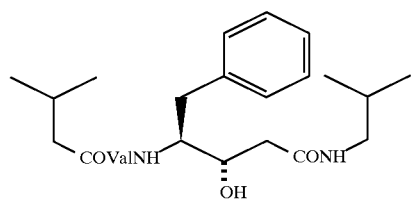

which has a $K_i$ of 1600 nM, (SEQ. ID. NO. 15);

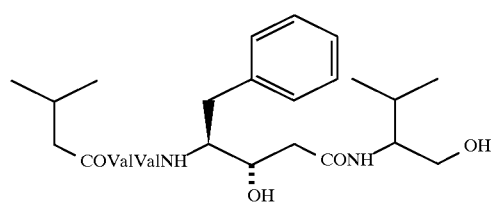

which has an IC$_{50}$ of 600 nM, (SEQ. ID. NO. 16);

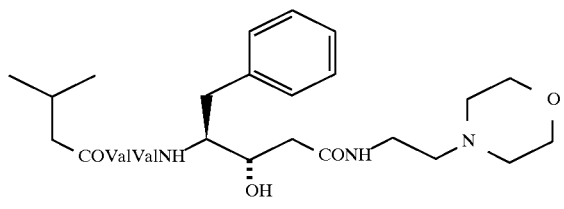

which has a K$_i$ of 1830 nM (SEQ.ID.NO. 17);

Specific, but not limiting examples of compounds of Formula (III) include:

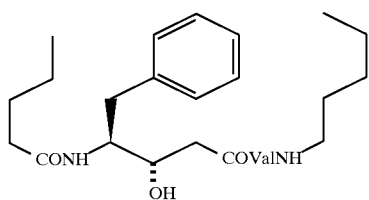

which has a K$_i$ of 400 nM, (SEQ. ID. NO. 18);

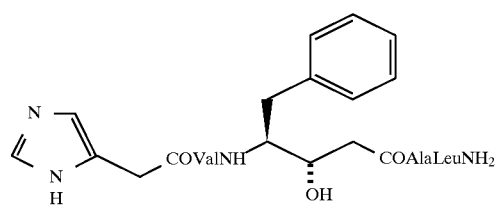

which has an IC$_{50}$ of 500 nM, (SEQ. ID. NO. 19);

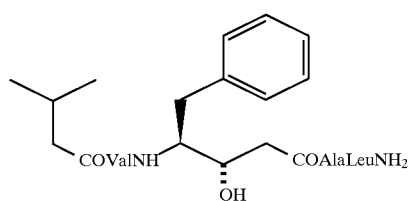

which has a K$_i$ of 8 nM, (SEQ. ID. NO. 20);

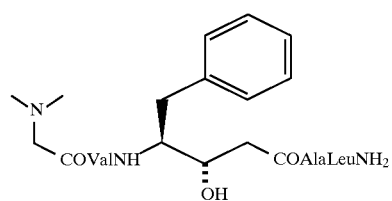

which has an IC$_{50}$ of 1000 nM, (SEQ. ID. NO. 21);

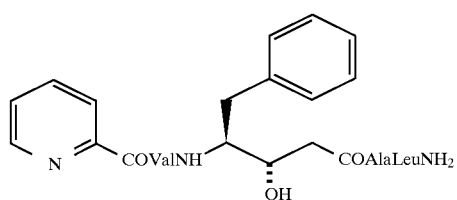

which has a K$_i$ of 21 nM, (SEQ. ID. NO. 22);

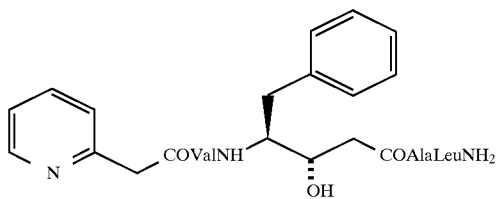

which has a K$_i$ of 20 nM, (SEQ. ID. NO. 23);

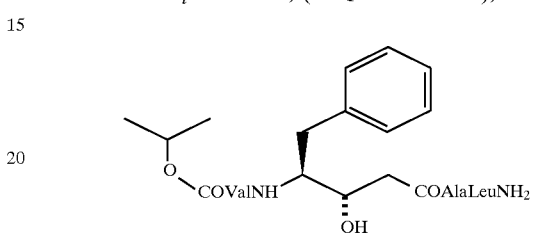

which has an IC$_{50}$ of 20 nM, (SEQ. ID. NO. 24);

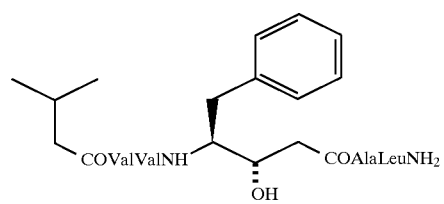

which has a K$_i$ of 0.18 nM, (SEQ. ID. NO. 25);

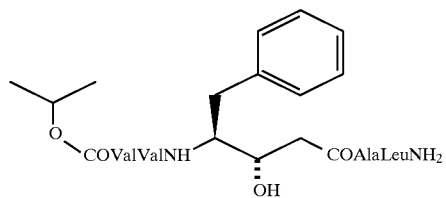

which has a K$_i$ of 0.24 nM, (SEQ. ID. NO. 26);

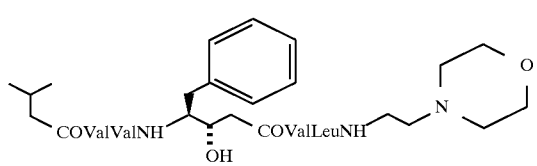

which has a K$_i$ of 0.14 nM, (SEQ. ID. NO. 27).

Specific examples of cyclic compounds within the scope of the present invention include:(Formula I:)

11
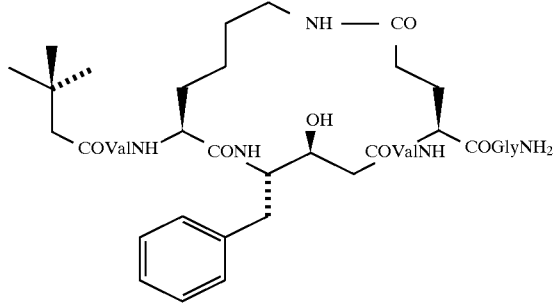
which has a $K_i$ of 1.4 nM, (SEQ. ID. NO. 28);
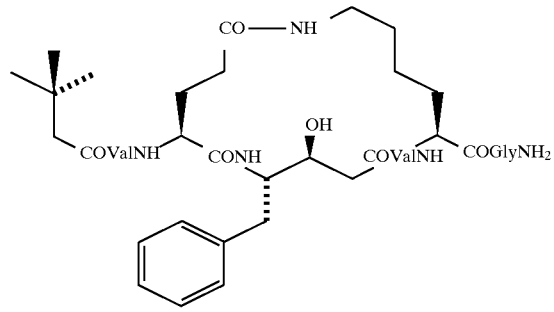
which has a $K_i$ of 2.3 nM, (SEQ. ID. NO. 29);
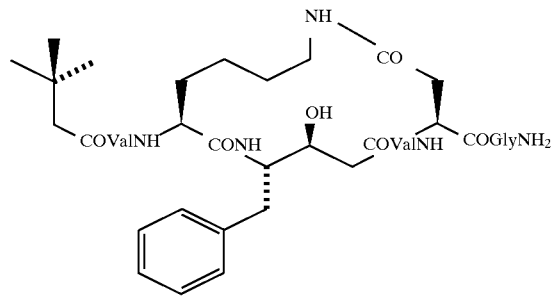
12
which has a $K_i$ of 12 nM, (SEQ. ID. NO. 30);
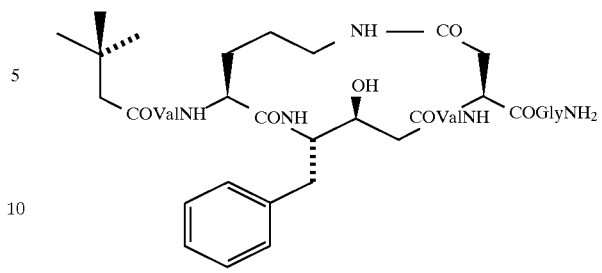
which has a $K_i$ value of 100 nM, (SEQ. ID. NO. 31);
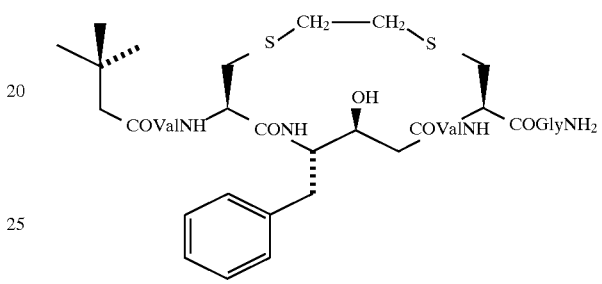
which has a $K_1$ value of 1.9 nM, (SEQ. ID. NO. 32);
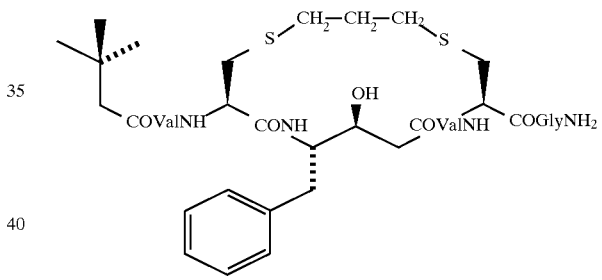
which has a $K_i$ value of 1.5 nM, (SEQ. ID. NO. 33);
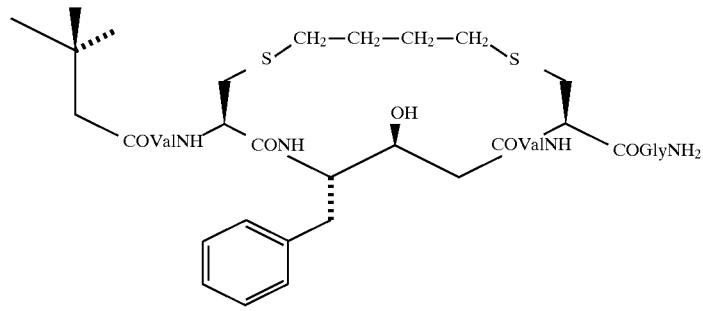

which has a $K_i$ value of 0.1 nM, (SEQ. ID. NO. 34);

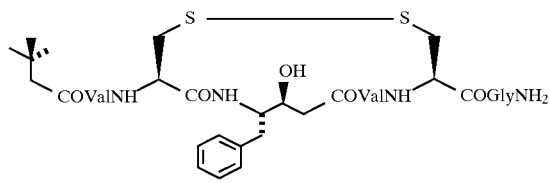

which has a $K_i$ value of 150 nM, (SEQ. ID. NO. 35);

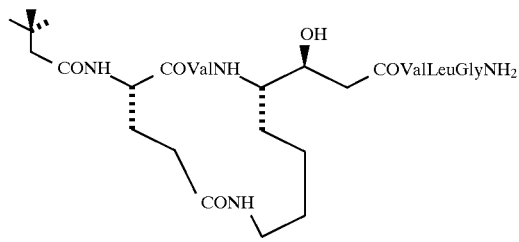

which has a $K_i$ value of 0.26 nM, (SEQ. ID. NO. 36);

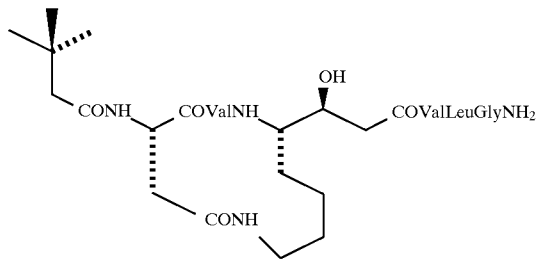

which has a $K_i$ value of 2.5 nM, (SEQ. ID. NO. 37);

Formula II:

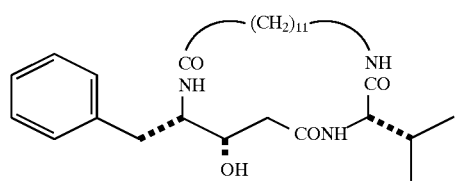

which has an $IC_{50}$ of 10,000 nM;

Formula IV:

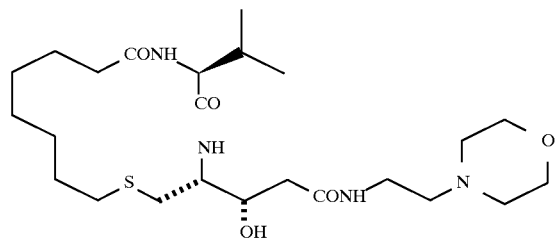

which has a $K_i$ value of 4 nM;

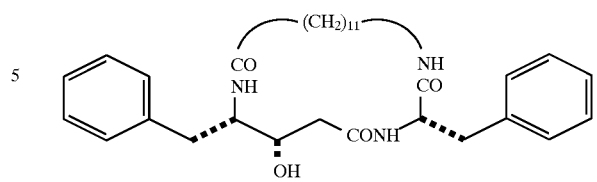

which has a $K_i$ value of 21 nM;

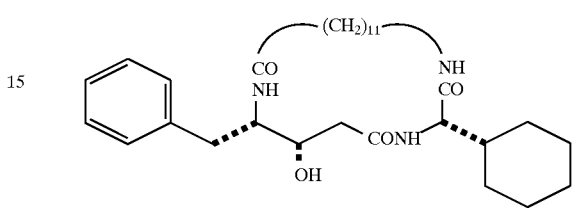

which has a $K_i$ value of 85 nM;

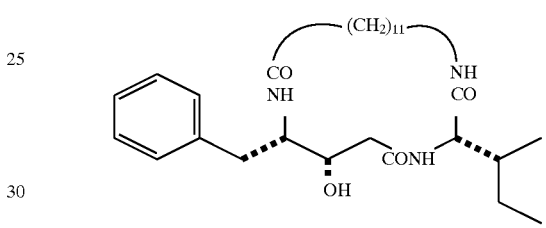

which has a $K_i$ value of 22 nM;

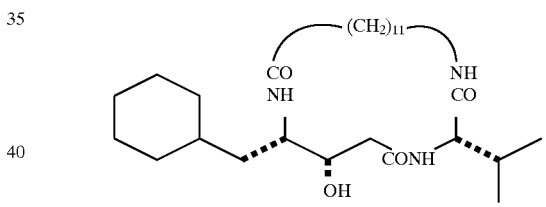

which has a $K_i$ value of 10 nM;

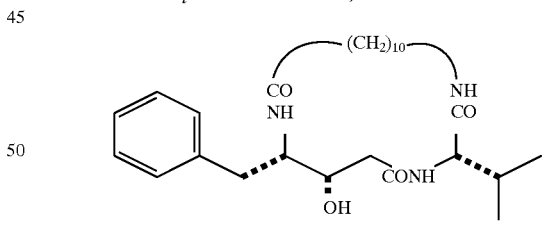

which has a $K_i$ value of 20 nM;

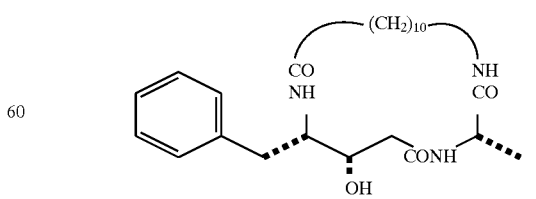

which has a Ki value of 140 nM.

The compounds of the present invention may exist in a free, i.e. unprotected, or protected form. The protected form herein refers to compounds wherein one or more reactive groups, e.g. amino groups or —OH groups, are substituted by a protecting group. Suitable protecting groups are any of those known in the art, such as acetyl, benzyloxycarbonyl and t-butoxycarbonyl.

The compounds of the present invention, whether they are in a free or protected form, may exist as salts or as complexes. Acid addition salts may be formed with organic acids, polymeric acids, and inorganic acids, for example. Such acid addition salt forms include inter alia the hydrochlorides and acetates. Complexes are herein defined as compounds of known type, formed on addition of inorganic substances, such as inorganic salts or hydroxides such as Ca- and Zn-salts, and/or on addition of polymeric organic substances.

The present invention further provides methods and compositions for preventing or treating diseases. Particular non-limiting examples of diseases include cancer including for example breast cancer, Alzheimer's disease, and malaria.

Specifically, this invention provides for the use of the compounds and compositions of the present invention to inhibit the activities of cathepsin D and plasmepsins I and II for treating and preventing diseases such as cancer, Alzheimer's disease, and malaria. The present invention also provides pharmaceutical compositions comprising the same.

The present invention further provides methods of preventing or treating a disease by the administration of a therapeutically effective amount of a cathepsin D or plasmepsin I or II inhibitor compound.

More particularly, the present invention provides methods of treating cancer by administration of a therapeutically effective amount of at least one cathepsin D inhibitor described herein which, for example, inhibits the invasion and metastasis of cancerous cells.

In addition, the present invention provides methods of treating Alzheimer's disease by administration of a therapeutically effective amount of at least one cathepsin D inhibitor described herein which, for example, inhibits the formation of senile plaques.

In addition, the present invention provides methods of treating malaria by administration of a therapeutically effective amount of a plasmepsin I or II inhibitor described herein which, for example, inhibits the degradation of hemoglobin by the malarial intracellular parasite.

The present invention also provides methods of preventing or treating diseases by the administration of a therapeutically effective amount of at least one compound of the present invention in combination with chemotherapeutic agents, toxins, or irradiation. Examples of chemotherapeutic agents are known to those skilled in the art and include, but are not limited to, bleomycin, mitomycin, cyclophosphamide, doxorubicin, paclitaxel, and cisplatin.

In one embodiment of the invention, the compounds of the present invention are administered in a pharmaceutically acceptable carrier. A pharmaceutically acceptable carrier encompasses any of the standard pharmaceutical carriers such as sterile solution, tablets, coated tablets and capsules. Such carriers may typically contain excipients such as starch, milk, sugar, certain types of clay, gelatin, stearic acid, talc, vegetable fats or oils, gums, glycols, or other known excipients. Such carriers may also include flavor and color additives and other ingredients.

In the practice of the methods of this invention, the amount of the enzyme inhibitor incorporated in the composition may vary widely. Methods for determining the precise amount depend upon the subject being treated, the specific pharmaceutical carrier, the route of administration being employed, the frequency with which the compound is to be administered, and whether the composition is administered in conjunction with a chemotherapeutic agent and/or irradiation treatment.

The present invention further provides a method of treating a subject afflicted with a tumor which comprises contacting the tumor with an amount of one of the cathepsin D inhibitors described herein which is administered to the subject previous to, simultaneous to, or subsequent to, administration of a chemotherapeutic agent or to an amount of irradiation effective to treat the tumor. The administration of the composition may be effected by any of the well known methods, including but not limited to, oral, intravenous, intramuscular, and subcutaneous administration.

Plasmepsin I and II are enzymes which are required for specific degradation of hemoglobin by the malarial intracellular parasite. Due to the high active site similarity between cathepsin D and plasmepsins, some of the cathepsin D inhibitors of the present invention are useful in preventing the growth of *Plasmodium falciparum*, a causative agent of malaria. Non-limiting examples of compounds which exhibit plasmepsin I or II (aspartic hemoglobinases from *Plasmodium falciparum*) inhibitory activity include the following:

(Formula I):

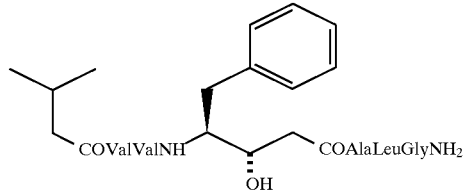

which has a PMI $K_i$=1.2 nM PMII $K_i$=0.1 nM;

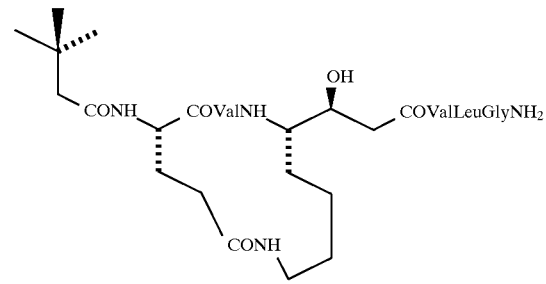

which has a PMI $K_i$=22 nM PMII $K_i$=0.2 nM;

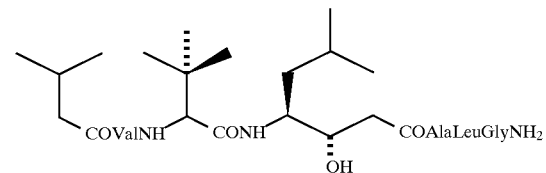

which has a PMI $K_i$=7 nM PMII $K_i$=3 nM;

(Formula III):

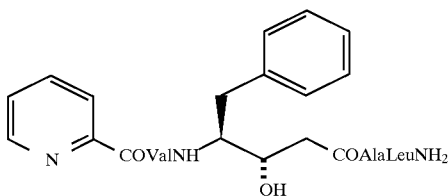

which has a PMI $K_i$=16 nM PMII $K_i$=0.9 nm.

SYNTHESIS:
LINEAR INHIBITORS:

The linear peptide inhibitors of the present invention were synthesized by the solid phase method using the Fmoc group for α-amino protection and acid labile groups for side chain protection of trifunctional amino acids e.g. [FmocCys(Trt)OH, FmocAsp(OtBu)OH and FmocGlu(OtBu)OH]. The aminomethyl polystyrene resin (Bachem California) was modified with acid labile linker Fmoc-2,4-dimethoxy-4'-(carboxymethoxy)-benzhydrylamine (Bachem Bioscience, Inc.) to a final substitution of 0.3–0.5 mmol/g. The Fmoc protected amino acids were coupled as HOBt esters, DIC (diisopropylcarbodiimide) was used for activation, and a 20% solution of piperidine in DMF (dimethyl formamide) for deprotection in each step. The Fmoc protected derivatives of statine and 3-hydroxy-4-amino-5-phenyl pentanoic acid (AHPPA or phenylstatine) were prepared according to the modified described procedure of Jouin, P. et al. *J. Chem. Soc. Perkin. Trans.* 1, 1177 (1987). The final cleavage of inhibitors from the resin was accomplished by treating with TFA (trifluoroacetic acid) containing 5% of water (and 3% of triethyl silane in the case of cysteine containing inhibitors). All the inhibitors were purified by reverse phase high performance liquid chromatography (HPLC) (column VYDAC C-18 2.5×25 cm) using water-acetonitrile mixtures containing 0.05% TFA in a gradient elution. Purity of all compounds was checked with analytical reverse phase HPLC (column CYDAC C-18 0.4×25 cm). All compounds gave correct molecular peaks in the mass spectrum (SIMS).

CYCLIC ANALOGS:
Preparation of Cyclic Disulfides.

The dibenzylated dithiol (100–500 mg) was dissolved in 150 ml of refluxing anhydrous liquid ammonia. Sodium metal was then added in small pieces to the solution until it remained blue. The addition was finished when the blue color persisted for 3 minutes. The mixture was then decolorized with a crystal of $NH_4Cl$ and ammonia was evaporated. The solid residue was suspended in 10% aq. $KHSO_4$ and the precipitated dithiol was filtered off. Yield is usually close to 100%.

The dithiol (30 mg) was dissolved in 30 ml of anhydrous degassed DMF containing 10 eq. of diisopropylethylamine (DIEA). A solution of 1.1 eq. of α,ωdihaloalkane in 5 ml of DMF was then added dropwise during 12 hours to the above solution. The mixture was left to stand for an additional 12 hours at room temperature. DMF was evaporated under reduced pressure and the obtained solid residue was washed with 5% aq. $NaHCO_3$ and ether. Yield 70–90% of crude cyclic inhibitor. The product was purified by preparative HPLC for the purpose of $K_i$ determination.
Other Cyclic Analogs Compounds related to Seq. ID number 42 but lacking the Ile can be prepared by condensing an N-protected statine analog with an ω-amino ester, hydrolyzing the ester, removing the N-protecting group of the statine, and cyclizing to form the lactam. Alternatively an ester of statine can be condensed with an N-protected ω-amino acid to provide the N-acylated statine which can be deprotected and cyclized to give the lactam.

Analogs such as in compounds of formula IV where a carboxamide is replaced with a sulfonamide or a phosphonamide may be prepared in an analogous way to the carboxamides, but in place of typical peptide coupling conditions, more vigorous activation of the sulfonic or phosphoric acid such as by preparing the sulfonyl or phosphoryl chloride may be required.

The amides described above can be replaced by hydrazides by using a suitably C-protected ω-hydrazino acid and condensing it with a suitably activated carboxylic or related acid derivative.

The oxygen of the carbonyl containing derivatives such as carboxamides may be replaced by sulfur by using such common thionating agents as $P_2S_5$ or Lawesson's reagent. The resulting thiocarbonyls can be converted into imino derivatives by treating with amines, in some cases after prior activation of the thiocarbonyl by, for example, alkylation.

BRIDGING GROUPS

It is recognized that the ω-amino acid may have up to 4 of its carbon atoms replaced by heteroatoms such as O, N, or S. These amino acids may be prepared by using methods known to those skilled in the art. For example a shorter chain ω-halo acid derivative can be reacted with an N-protected amino alcohol, aminoalkanethiol, or diamine to provide an ω-amino acid with an O, S, or N beta to the amino terminus. Similarly an ω-hydroxy acid could be derivatized as, for example, a sulfonate, and a similar displacement reaction run. Alternatively a suitably protected shorter chain ω-amino, hydroxy, or sulfhydryl acid could be derivatized, for example, by reaction with a suitably N-protected amino alkyl halide or sulfonate. Similarly it is recognized that replacing a sulfonate or halide in the above alkylations by an epoxide would allow formation of chains with hydroxyl substituents. It should be noted that chains containing heteroatoms need not be synthesized only by using alkylation type chemistry. Chains containing an amide bond can be synthesized, for example, by reacting an amino acid with another amino acid using standard peptide coupling conditions to generate the ω-amino acid required. Furthermore an O-protected ω-amino acid could be reacted with a phosgene equivalent to provide an isocyanate which could then be reacted with an N-protected amino alcohol or diamine to provide a urethane or urea-substituted chain.

It is recognized that the chain need not be built up separately, but may be formed by attaching pieces of the chain to the amino and carboxy ends of the molecule and then connecting them in some way. This approach is exemplified in Seq. ID numbers 32–34, where the two cysteine substituents are connected by a dihalide to form the desired bridge compounds. Similarly Seq. ID. NO. 28 can be prepared by cyclization of a compound with an amino alkyl substituent at one end and a carboxy alkyl substituent at the other to give the chain containing an amide functionality.

It should be noted that chains where carbon atoms have been replaced by heteroatoms are amenable to further chemistry which can also lead to active compounds. For example sulfides can be converted by peracids to sulfoxides or sulfones. Secondary amines can be alkylated or acylated.

Chains containing oxo or hydroxy substitution can also be elaborated. For example oxo groups may be condensed with amines, hydrazines, hydroxylamine, alkoxyamines, phosphorous pentasulfide, diethylamino sulfur trifluoride (DAST), alkylidene triphenyl phosphoranes or the like to provide imines, hydrazones, oximes, thiones, difluoromethylenes, alkylidenes and the like. Reduction provides alcohols, or methylenes. Alcohols may be converted into halides for example by phosphorous trihalide, oxidized to oxo compounds, acylated to give esters or alkylated to give ethers.

The chain could also incorporate unsaturation such as one or more double or triple bonds. These can be generated by elaboration of saturated analogs, such as, for example, by elimination of an alcohol derivative such as a xanthate ester, or a halide. Alternatively the unsaturation can be present in one of the precursors for the chain. For example an unsaturated fatty acid could be converted to an ω-amino unsaturated acid, for example, via the ω-bromo derivative. This material could then be used to form the ring as described for the saturated analogs. It should be noted that compounds containing unsaturation in the ring are amenable to further transformation. Cycloadditions such as Diels-Alder reactions, 1,3-dipolar additions, and 2+2 cycloadditions lead to bridged 6-, 5-, and 4-membered ring systems. Three membered rings can be generated by carbene reactions, epoxidations with, for example, peracids, and aziridinations. Alternatively the ring can be part of the ω-amino acid before attachment to the core. Thus, for example, ω-aminoalkyl benzoic acids could be utilized to form the chain.

Carbamates, thiocarbamates and ureas at Y may be generated by reacting the C-protected amino acid core with a phosgene equivalent such as trichloroacetyl chloride followed by a mono N-protected ω-diamine, ω-amino alcohol, or ω-amino thiol. Similarly sulfamides can be generated by replacing the phosgene equivalent by sulfuryl chloride, or an equivalent.

Compounds of formula IVa may be generated by replacing the amino acid core in IV by a diamine or equivalent. One way this can be accomplished is by taking a suitably N-protected amino acid, forming an active ester, displacing by $NaN_3$ to form the acyl azide, and then heating to form the isocyanate. Reaction with mono N-protected αdiamines, ω-amino alcohols, or ωamino thiols as above provides carbamates, thiocarbamates and ureas at X. Alternatively, the isocyanate can be hydrolyzed to give the amine which can be acylated to form amide derivatives. Similarly, sulfonylation can provide sulfonyl analogs.

Compounds of formula IVb replace the amine at X in IVa by oxygen or sulfur. These compounds can be synthesized, for example, by using phenylalaninal as the starting material. Conversion of the aldehyde to the epoxide may be accomplished either directly with an appropriate ylide, or indirectly via Wittig olefination followed by epoxidation, for example, with a peracid. The epoxide can then be reacted with a suitable alcohol or thiol to provide a diol or mercapto alcohol respectively. Acylation of these moieties, with for example a suitable isocyanate provides the X functionality described in IVb.

Compounds of formula V may be prepared in a similar fashion as those for formula IV but using an optionally α-alkylated homostatine core rather than a statine core. Homostatine analogs can be synthesized, for example, by activating the carboxylic acid of a protected statine analog, reacting with diazomethane to generate the diazoketone, and then subjecting it to Wolff rearrangement using thermal, photochemical, or metal-catalyzed conditions. The resulting carboxylic acid can then be elaborated as in formula IV.

Compounds of formula Va have the amide of X in formula V reversed. Such compounds are available from derivatives of statine. Thus a statinal derivative can be reductively aminated to give the required precursor amine which can then be acylated, sulfonylated, or phosphorylated as for previously described examples. Alternatively the amine could be synthesized by reduction of a statine amide or reaction of an activated statinol derivative with an amine equivalent.

Similarly, compounds of formula Vb can be derived from statinol analogs by acylation on oxygen with, for example, an isocyanate derivative. Alternatively, the alcohol can be activated as, for example, a sulfonate derivative and then reacted with a thiol to give the sulfur analogs.

The Examples herein are meant to exemplify the various aspects of carrying out the invention and are not intended to limit the scope of the invention in any way.

EXAMPLE 1

The synthesis of this inhibitor is represented in Scheme A below:

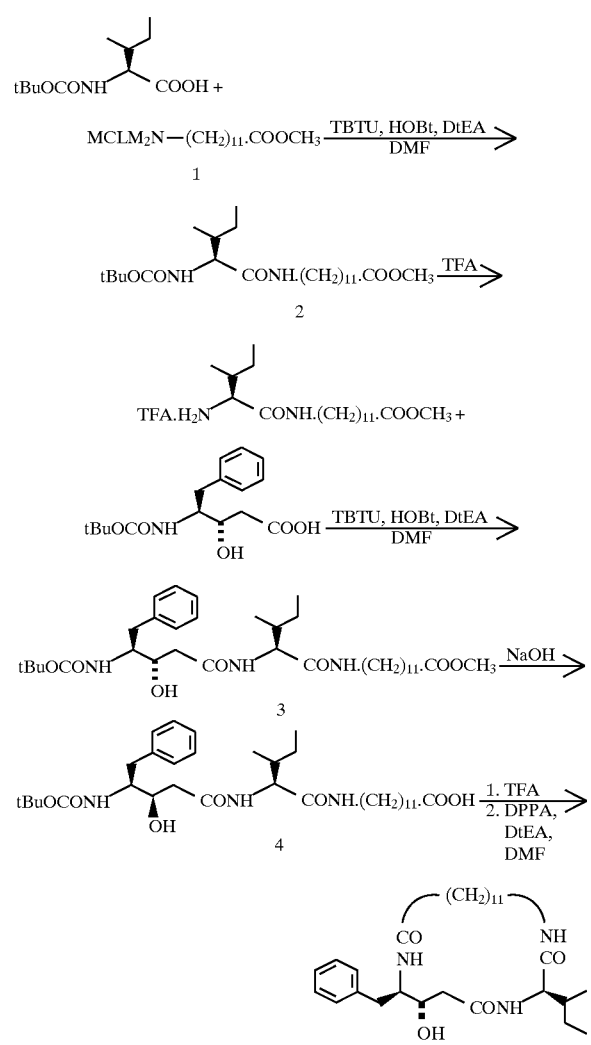

The various compounds shown in scheme A can be prepared as follows:

12-aminododecanoic acid methylester hydrochloride (1)

To the suspension of 12-aminododecanoic acid (2.15 g; 10 mmol) in 2,2-dimethoxypropane (100 ml) was added 36% aqueous HCl (10 ml) and the mixture was treated in an ultrasonic bath until all solid material was dissolved. The mixture was then left to stand overnight, concentrated to dryness, dissolved in 40 ml of methanol and precipitated with approximately 500 ml of dry ether to give 2.4 g of 1 (90.5% yield).

12-(t-Butyloxycarbonylisoleucinyl)-aminododecanoic acid methylester (2)

Boc-Ile-NH—$(CH_2)_{11}$—$COOCH_3$

Boc (t-butyloxycarbonyl)-Ile (isoleucine)—OH.1/2$H_2O$ (384 mg; 1.6 mmol), HCl.$H_2N$—$(CH_2)_{11}$—$COOCH_3$ (1) (398 mg; 1.5 mmol), HOBT (N-hydroxybenzotriazole) (260 mg; 1.7 mmol) and TBTU (2-(1H-benzotriazol-1-yl)-1,1,3,3-tetramethyluronium tetrafluoroborate)) (546 mg; 1.7 mmol) were dissolved in DMF (5 ml). DIEA (diisopropylethylamine) (860 µl; 5 mmol) was added to the above solution and the mixture was left to stand overnight. Five drops of N-aminoethylmorpholine were then added to the solution. After 30 minutes DMF was removed in vacuo and the solid residue suspended in 10% aqueous $KHSO_4$ (20 ml). The precipitate was filtered off, washed with water, 5 % aqueous $NaHCO_3$, water again, and then dried in a vacuum desiccator to give 630 mg of 2 (95 % yield).

12-(t-Butyloxycarbonyl-phenylstatinyl-isoleucinyl)-aminododecanoic acid methylester (3)

Boc-Pst-Ile-NH—$(CH_2)_{11}$—$COOCH_3$

Boc-Ile-$(CH2)_{11}$—$COOCH_3$ (2) (384 mg; 0.8 mmol) was dissolved in TFA (trifluoroacetic acid) (3 ml). After 30 minutes of standing at room temperature, the TFA was removed in vacuo, the oily residue was concentrated three more times with ether to remove the remaining TFA, and then dissolved in 5 ml of DMF.Boc-Pst-OH (247 mg; 0.8 mmol), TBTU (289 mg; 0.9 mmol) and DIEA (1030 µl; 6 mmol) were added to the above solution and the mixture was left to stand overnight. Workup as for 2 yielded 492 mg of 3 (97%).

12-(t-Butyloxycarbonyl-phenylstatinyl-isoleucinyl) aminododecanoic acid (4)

Boc-Pst-Ile-NH—$(CH_2)_{11}$—COOH

Boc-Pst-Ile-NH—$(CH_2)_{11}$—$COOCH_3$ (3) (380 mg; 0.6 mmol) was dissolved in a mixture of 1,4 dioxane (5 ml) and methanol (1 ml) and combined with 1N aqueous solution of NaOH (1.5 ml). The reaction was complete in approximately two hours. The organic solvents were evaporated and the remaining aqueous slurry was acidified with 10% aqueous $KHSO_4$ (10 ml). The precipitate was filtered off, washed with water, and dried in a vacuum desiccator to yield 353 mg of 4 (95% yield).

Cyclo-12-aminododecanoyl-phenylstatinyl-isoleucinyl (5)

—CO—Pst-Ile-NH—$(CH_2)_{11}$—

Boc-Pst-Ile-NH—$(CH_2)_{11}$—COOH (4) (248 mg; 0.4 mmol) was deprotected with TFA as described for 3 and dissolved in DMF (20 ml). This solution was added dropwise to a stirred solution of DPPA (diphenyl phosphorylazide) (1.1 g; 4 mmol) and DIEA (1.38 ml; 8 mmol) in DMF (100 ml) over the course of 17 hours via syringe pump. The mixture was then stirred for an additional 3 hours, evaporated to dryness and triturated with ether. The precipitated product was filtered off, washed with ether, 5% aqueous $NaHCO_3$, and water and then dried in a vacuum desiccator to provide 160 mg of crude 5 (80% yield). For the purpose of biological testing, the product was purified by RP-HPLC.

SIMS MS $M^+Na^+$524

EXAMPLE 2

An alternate sequence to a cyclic inhibitor is represented in Scheme B below:

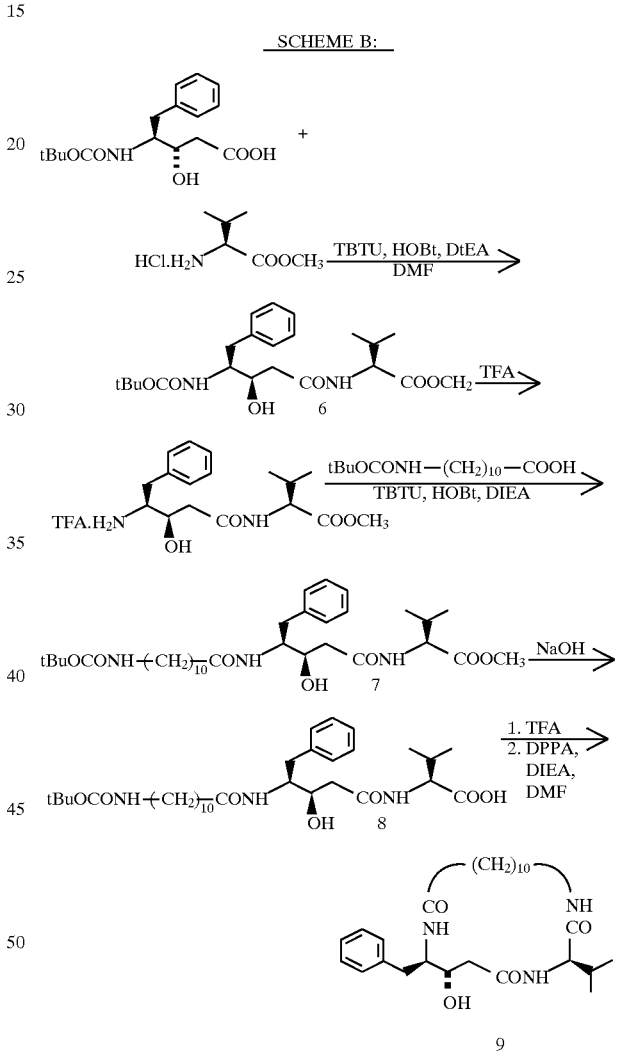

t-Butyloxycarbonyl-phenylstatinyl valine methylester (6)

Boc-Pst-Val-$OCH_3$

Boc-Pst-OH (309 mg; 1 mmol), HCl.H—Val$OCH_3$ (184 mg; 1.1 mmol) and TBTU (385 mg; 1.2 mmol) were dissolved in 5 ml of DMF and DIEA (688 µl; 4 mmol) was added to the solution. The mixture was left to stand overnight and then evaporated to dryness. The oily residue was dissolved in ethylacetate and the ethylacetate solution was washed with 10% aqueous $KHSO_4$, water, 5% aqueous $NAHCO_3$, and water again, dried over $MgSO_4$, and concentrated to give 420 mg of 6.

11-t-Butyloxycarbonyl-aminoundecanoyl-phenylstatinyl valine methyl ester (7)

Boc-NH—(CH$_2$)$_{10}$—CO—Pst-Val-OCH$_3$

Boc-Pst-Val-OCH$_3$ (420 mg; 1 mmol) was deprotected with TFA as described for 3. After addition of ether, a precipitate of TFA.H-Pst-Val-OCH$_3$ (349 mg; 0.8 mmol) was obtained. This was dissolved in 5 ml of DMF together with Boc-NH—(CH$_2$)$_{10}$—COOH (241 mg; 0.8 mmol), TBTU (289 mg; 0.9 mmol) and DIEA (516 µl; 3 mmol). After 10 hours of standing at room temperature, DMF was removed in vacuo, the residue dissolved in ethylacetate and worked up as described above for 6 to yield 480 mg of oily 7.

11-t-Butyloxycarbonyl-aminoundecanoyl-phenylstatinyl valine (8)

Boc-NH—(CH$_2$)$_{10}$—CO—Pst-ValOH

Hydrolysis of crude Boc-NH(CH$_2$)$_{10}$—CO—Pst-ValOCH$_3$ (7) (480 mg; 0.8 mmol) as described above for 4 provided 435 mg of oily 8.

Cyclo-11-aminoundecanoyl-phenylstatinyl-valine (9)

—CO—Pst-Val-NH—(CH2)$_{10}$—

Boc-NH—(CH$_2$)$_{10}$—CO—Pst-ValOH (8) was deprotected and cyclized using the procedure described for 5. Yield 260 mg (55% from Boc-Pst-OH used in 6) of crude solid 9. For the purpose of biological testing the product 9 was purified by RP-HPLC.SIMS MS MH$^+$474

Example 3

Solid phase synthesis of a cyclic inhibitor.

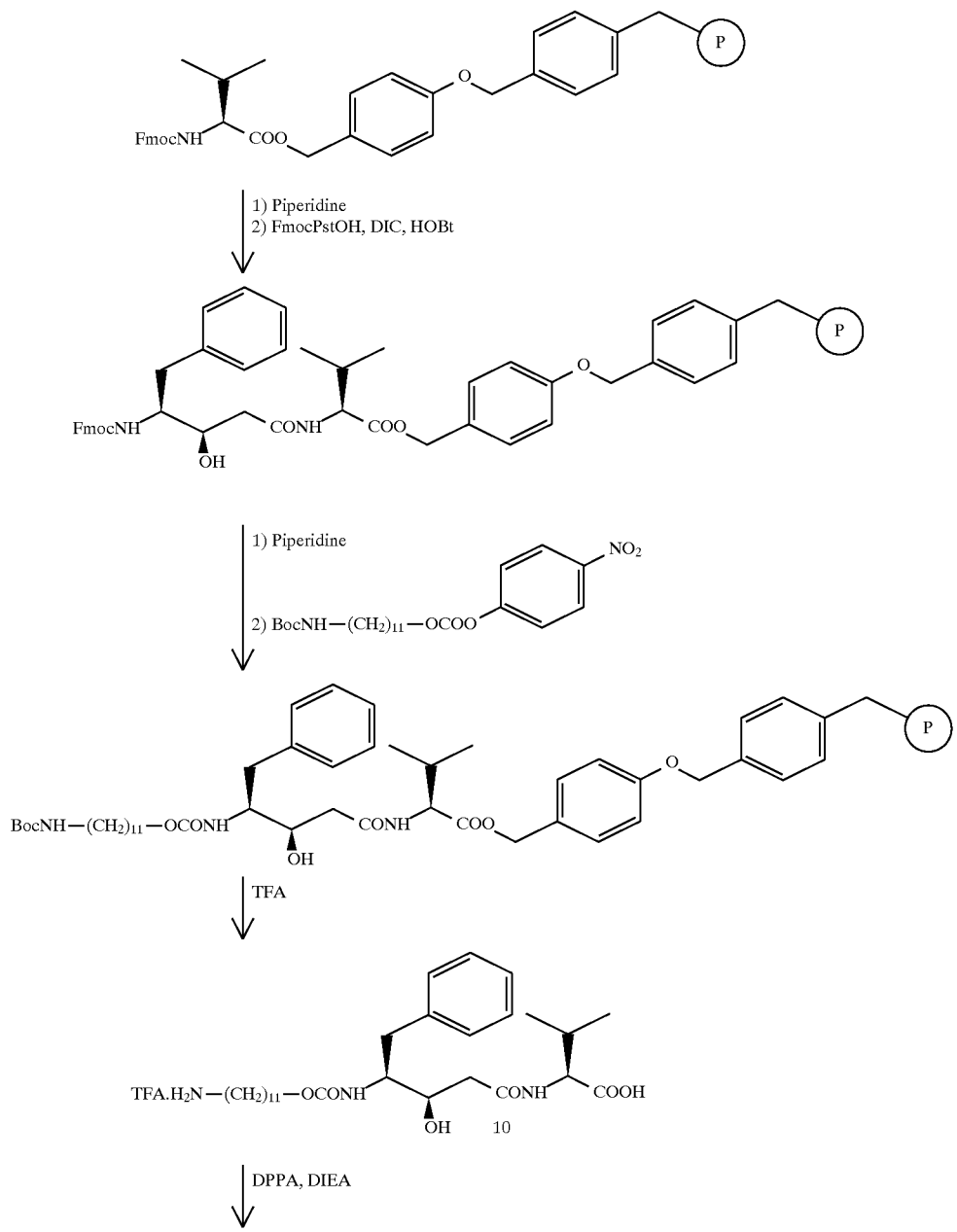

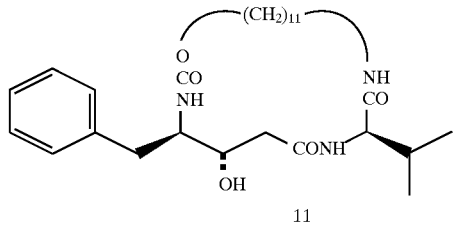

(SEQ. ID. NO. 48)

Solid Phase Synthesis of TFA,H$_2$N—(CH$_2$)$_{11}$—OCOPstVal-OH (10)

FmocVal-WANG-resin (1g, 0.37 mmol) was swollen in DMF, washed with DMF (3×2 min), deprotected with 20% piperidine in DMF (1×2 min; 1×20 min) and washed again with DMF (5×2 min). FmocPstOH (319 mg, 0.74 mmol) was then coupled using DIC (diisopropylcarbodiimide) (101 mg, 0.8 mmol) and HOBt (122 mg, 0.8 mmol) for activation. The resulting resin was then deprotected and washed as described above. The solution of BocNH—(CH$_2$)$_{11}$—COO-pC$_6$H$_4$—NO$_2$ (452 mg, 1 mmol) and DIEA (190 μl, 1.1 mmol) in 5 ml of DMF was added and the mixture was shaken overnight. The resin was washed with DMF (5×2 min), 20% piperidine in DMF (2×2 min), DMF (3×2 min), pyridine-DCM (1:1) (3×2 min) and DCM (dichloromethane) (5×2 min). The product was then cleaved off the resin with 95% TFA (2×30 min) and the resin was washed with DCM (5×2 min). The combined solutions were evaporated to dryness. The oily residue (200 mg) was used directly for the next reaction.

Synthesis of (11) (cyclization)

TFA.H$_2$N—(CH$_2$)$_{11}$—COPstVal-OH(10) was cyclized using the procedure described for 5. Yield 40 mg (21.5% based on the resin substitution) of crude 11. For the purpose of biological testing the product was purified by RP—HPLC. Product was characterized by SIMS—MS, M+H$^+$=504, M+Na$^+$=526.

Compound 11 has a K$_1$ against cathepsin D of 3.6 nM.

Example 4 Synthesis of a cyclic urea.

Synthesis of Inhibitor 15

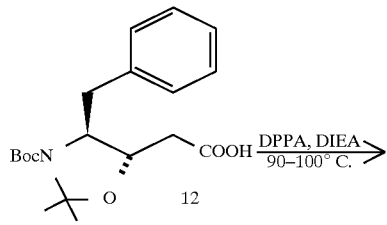

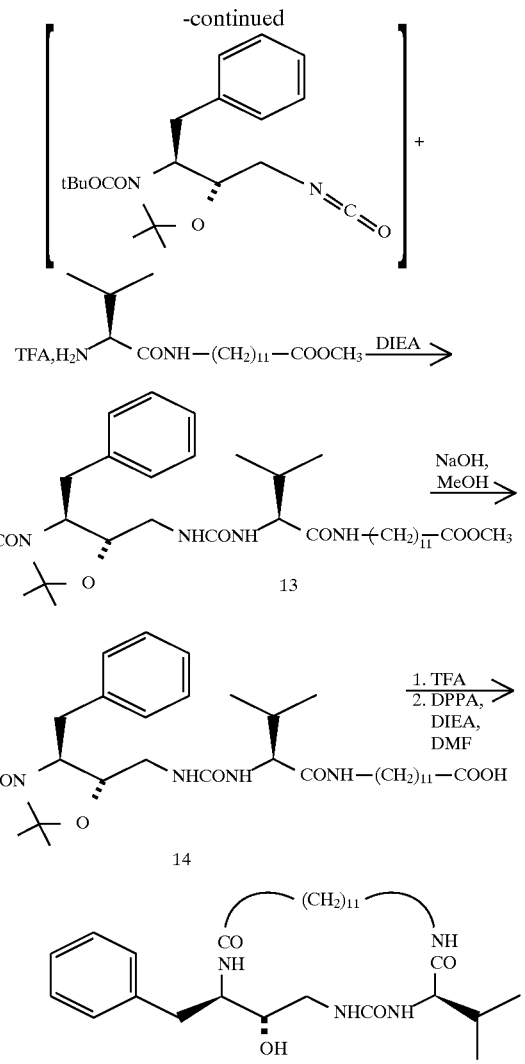

(SEQ. ID. NO. 49)

Synthesis of 13

Boc-Pst(acetonide)OH (850 mg, 2.44 mmol) was dissolved in 13 ml of toluene and approx. 2–3 ml of toluene was distilled off to dry the solution. DPPA (1 g, 3.66 mmol) and DIEA (0.84 ml, 4.88 mmol) were added and the mixture was heated to 90–100° C. for 2 hours. A solution of TFA.H—ValNH—(CH$_2$)$_{11}$—COOMe prepared from 1.2 g (2.8 mmol) Boc-ValNH(CH$_2$)$_{11}$CO$_2$Me and DIEA (1.46 ml, 8.5 mmol) in 3 ml of dry toluene was added to the reaction mixture, the mixture was heated for an additional 30 min and then left to stand overnight at room temperature. The toluene was removed in vacuo, the residue dissolved in ethyl acetate and washed subsequently with 10% aq.KHSO$_4$, brine, 5% NaHCO$_3$, brine, and finally dried with MgSO$_4$. The ethyl acetate was then removed in vacuo and the oily residue purified by flash chromatography in hexane-ethyl acetate (3:2). Yield 873 mg, 53% of 13. Product was characterized by SIMS–MS, M+H$^+$=675.

Synthesis of 14

13 (850 mg, 1.26 mmol) was hydrolyzed with NaOH according to the procedure described above for 4. Yield 850 mg (~100%) of oily 14, that was used directly for the next reaction.

Synthesis of 15 (Cyclization)

This compound was prepared using the procedure described above for 5. Yield 438 mg (69% calculated from 13). Product was characterized by SIMS–MS, M+H$^+$=503. Compound 15 has a K$_1$ against cathepsin D of 45 nM.

Inhibition Assays

Kinetic measurements.

Fluorogenic substrates Ac-Glu-Glu(EDANS)—Lys-Pro-Ile-Cys-Phe-Phe-Arg-Leu-Gly-Lys(DABCYL)—Glu-NH2 and Ac-Glu-Glu(EDANS)—Lys-Pro-Ile-Cys-Phe-Leu-Arg-Leu-Gly-Lys(DABCYL)—Glu-NH2 were used for measuring the activity of cathepsin D and plasmepsin 2 correspondingly. Typically, 485 μl of 50 mM Gly-HCl buffer, pH 3.5 (in the case of cathepsin D), or 100 mM sodium acetate buffer, pH 5.0 (in the case of plasmepsin 2), was mixed with 5 μl of DMSO and 5 μl of titrated protease (final concentration 0.2–10 nM) and incubated 3 min at 37° C. The reaction was initiated by the addition of 5 μl of substrate stock solution in DMSO. Increase in fluorescence intensity at the emission maximum of 487 nm (excitation wavelength was 349 nm) was monitored as a function of time using an Aminco Bowman-2 luminescence spectrometer (SLM Instruments, Inc.).

Plasmepsin 1 assays were run similarly to plasmepsin 2, using the fluorogenic substrate DABCYL-Gaba-Glu-Arg-Met-Phe-Leu-Ser-Pro-Gaba-Glu(EDANS)—NH2.

The initial rate of hydrolysis was calculated by a second degree polynomial fit using SLM AB2 2.0 operating software. Kinetic parameters were determined by nonlinear regression fitting of initial rate versus substrate concentration data to the Michaelis-Menten equation using the program Enzfitter version 1.05 (Leatherbarrow, R. J. 1987. Enzfitter, a program for non-linear regression analysis. Elsevier Scientific, New York).

For inhibition studies inhibitors were prepared as stock solutions at different concentrations in DMSO. In a typical experiment 485 μl of the appropriate buffer was mixed with 5 μl of inhibitor stock solution and 5 μ of titrated protease (final concentration 0.2–10 nM) and preincubated 3 min at 37° C. The reaction was initiated by the addition of 5 μl of substrate stock solution in DMSO. For data analysis the mathematical model for tight-binding inhibitors (Williams, J. W., and Morrison, J. F. *Methods Enzymol.* 63:437 (1979)) was used. The data were fitted by nonlinear regression analysis to the equation $$V=V_0/2E_t(\{[K_1(1+S/K_m)+I_t-E_t]^2+4K_i(1+S/K_m)E_t\}^{1/2}-[K_i(1+S/K_m)+I_t-E_t])$$

with the program Enzfitter (version 1.05), where V and V$_O$ are initial velocities with and without inhibitor, K$_m$ is a Michaelis-Menten constant and S, E$_t$ and I$_t$ are the concentrations of substrate, active enzyme and inhibitor respectively.

Although the foregoing invention has been described in some detail by way of illustration and example for purposes of clarity of understanding, it will be obvious to those skilled in the art that certain changes and modifications may be practiced without departing from the spirit and scope thereof as described in the specification and as defined in the appended claims.

What is claimed is:

1. A compound of the formula IV:

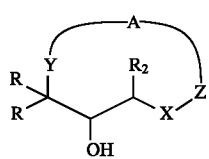

where X=CWNR, NRCW, $S(0)_n$NR, $NRS(O)_n$, P(0) (Q)NR, NRP(O) (Q), OCWNR, SCWNR; W=0, S, NR; n=0, 1, 2;
    Q=R, OR, $N(R)_2$;
    Y=NRCW, NRS(0) n, NRP(O)(Q);
    Z=CRR', NR, O, S;
    A=an optionally substituted bridging group which is saturated or unsaturated and having 2–15 atoms comprised of any stable combination of C, N, O, or S;
    R=hydrogen, alkoxycarbonyl, aralkoxycarbonyl, alkylcarbonyl, cycloalkylcarbonyl, cycloalkylalkoxycarbonyl, cycloalkylalkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, mono- and di-substituted aminocarbonyl and mono- and di-substituted aminoalkyl, alkoxyalkyl, alkylthioalkyl, mono- and di-substituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is di-substituted, said substituents along with the nitrogen atom to which they are attached form a heterocycloalkyl or heteroaryl radical; and R', $R_2$=H, halo, optionally substituted lower alkyl, lower alkoxy, lower alkylthio, mono- or di-lower alkyl amino;

with the proviso that when X=CONR and Y=NRCO, there is no more than one amide group, CONR or NRCO, in the bridging portion of A.

2. The compound of claim 1, wherein X, Y=NRCW, $NRS(O)_n$, NRP(O)(Q) and; Z=CRR',NR,O,S.

3. The compound of claim 1, wherein X=OCWNR, SCWNR; Y=NRCW, $NRS(O)_n$, NRP(O)(Q) and; Z=CRR', NR.

4. The compounds of claim 1, which are selected from the group consisting of

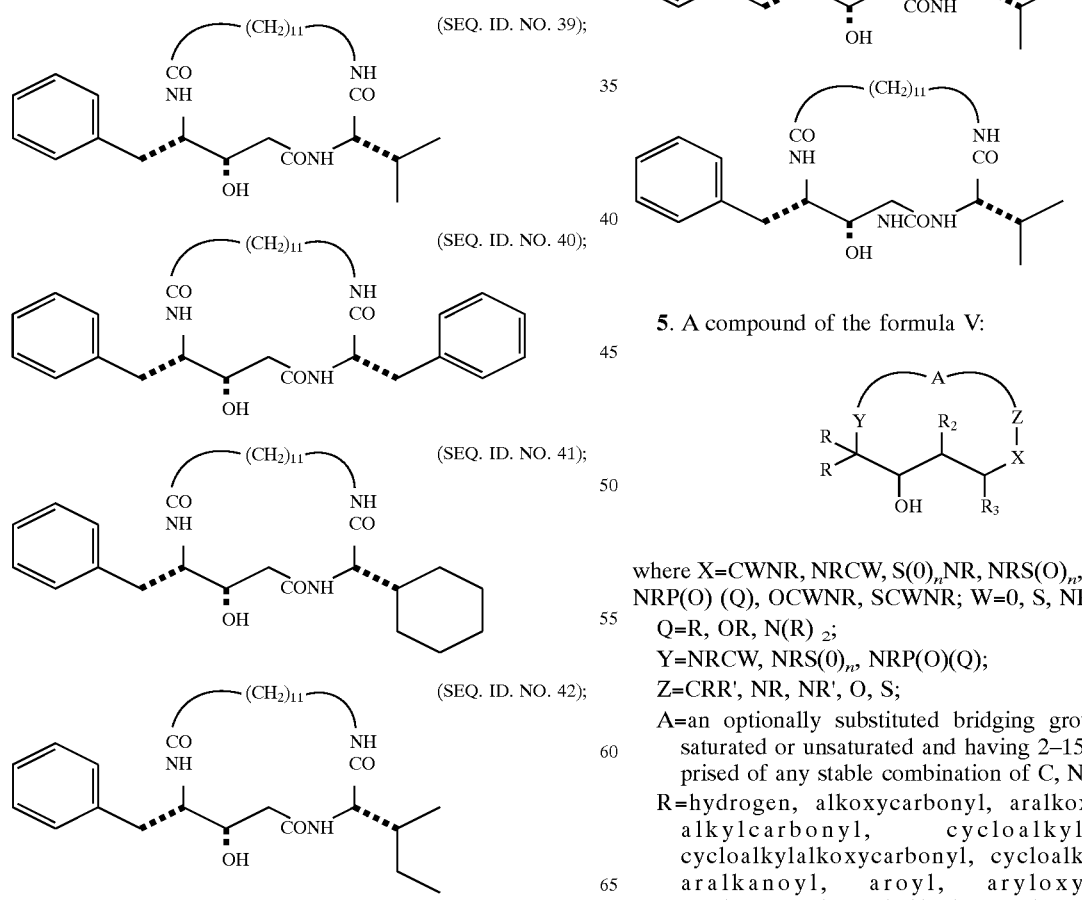

5. A compound of the formula V:

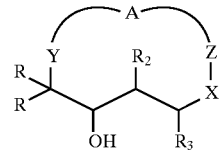

where X=CWNR, NRCW, $S(0)_n$NR, $NRS(O)_n$, P(0) (Q)NR, NRP(O) (Q), OCWNR, SCWNR; W=0, S, NR; n=0, 1, 2;

Q=R, OR, $N(R)_2$;

Y=NRCW, $NRS(0)_n$, NRP(O)(Q);

Z=CRR', NR, NR', O, S;

A=an optionally substituted bridging group which is saturated or unsaturated and having 2–15 atoms comprised of any stable combination of C, N, O, or S;

R=hydrogen, alkoxycarbonyl, aralkoxycarbonyl, alkylcarbonyl, cycloalkylcarbonyl, cycloalkylalkoxycarbonyl, cycloalkylalkanoyl, aralkanoyl, aroyl, aryloxycarbonyl, aryloxycarbonylalkyl, aryloxyalkanoyl, heterocyclylcarbonyl, heterocyclyloxycarbonyl, heterocyclylalkanoyl, heterocyclylalkoxycarbonyl, heteroaralkanoyl, heteroaralkoxycarbonyl, heteroaryloxycarbonyl, heteroaroyl, alkyl, alkenyl, cycloalkyl, aryl, aralkyl, aryloxyalkyl, heteroaryloxyalkyl, hydroxyalkyl, aminocarbonyl, aminoalkanoyl, mono- and di-substituted aminocarbonyl and mono- and di-substituted aminoalkyl, alkoxyalkyl, alkylthioalkyl, mono- and di-substituted aminoalkanoyl radicals wherein the substituents are selected from alkyl, aryl, aralkyl, cycloalkyl, cycloalkylalkyl, heteroaryl, heteroaralkyl, heterocycloalkyl, heterocycloalkylalkyl radicals, or where said aminoalkanoyl radical is di-substituted, said substituents along with the nitrogen atom to which they are attached form a heterocycloalkyl or heteroaryl radical; and R', $R_2$, and $R_3$ =H, halo, optionally substituted lower alkyl, lower alkoxy, lower alkylthio, mono- or di-lower alkyl amino.

6. The compound of claim 5, wherein X, Y=NRCW, NRS(O)$_n$, NRP(O)(Q); Z=CRR', NR, O, S.

7. The compound of claim 5 wherein X=OCWNR, SCWNR; Y=NRCW, NRS(O)$_n$, NRP(O)Q; Z=CRR', NR'.

8. The compounds of any one of claims 2, 3, 4, 6, 7, 1, or 5 in the form of an acid addition salt or complex thereof.

9. A pharmaceutical composition comprising at least one compound from any one of claims 2, 3, 4, 6, 7, 1, or 5 and a pharmaceutically acceptable carrier.

10. A method of inhibiting cathepsin D, plasmepsin I or plasmepsin II, which comprises contacting an environment containing cathepsin D, plasmepsin I or plasmepsin II with an inhibiting effective amount of at least one compound from any one of claims 2, 3, 4, 6, 7, 1, or 5.

* * * * *